United States Patent [19]

Davies et al.

[11] 4,372,962
[45] Feb. 8, 1983

[54] CLAVULANIC ACID DERIVATIVES THEIR PREPARATION AND USE

[75] Inventors: John S. Davies; Gerald Brooks, both of Reigate, England

[73] Assignee: Beecham Group Limited, England

[21] Appl. No.: 149,322

[22] Filed: May 13, 1980

[30] Foreign Application Priority Data

May 17, 1979 [GB] United Kingdom ............... 7917210

[51] Int. Cl.³ .................. C07D 498/04; A61K 31/42
[52] U.S. Cl. .................................. 424/272; 260/245.3
[58] Field of Search ..................... 260/245.3; 424/272

[56] References Cited

U.S. PATENT DOCUMENTS 4,215,128 7/1980 Howarth ............................ 424/272

OTHER PUBLICATIONS

"IUPAC Nomenclature", pp. 475-477.
Cherry et al., Chem. Abs. 88, 6861v, (1977).
Cherry et al., Chem. Ab. 58, 190803b, (1978).

Primary Examiner—Mark L. Berch
Attorney, Agent, or Firm—Jacobs & Jacobs

[57] ABSTRACT

The compounds of the formula (I):

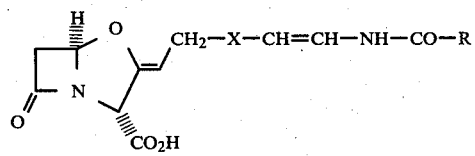

and pharmaceutically acceptable salts and in-vivo hydrolysable esters thereof wherein X is a sulphur atom or SO or $SO_2$ group and R is a hydrogen atom or an alkyl group of 1 to 6 carbon atoms have been found to be β-lactamase inhibitors and antibacterial agents. Their preparation and use is described.

120 Claims, No Drawings

CLAVULANIC ACID DERIVATIVES THEIR PREPARATION AND USE

This invention relates to novel antibiotics and β-lactamase inhibitors and to processes for their production.

Belgian Patent Specification Nos. 850779 and 851821 disclose that thioethers derived from clavulanic acid and oxidation products of such thioethers possess β-lactamase inhibitory properties. It has now been found that a small class of thioethers and their oxidation products are particularly effective in enhancing the effectiveness of penicillins and cephalosporins in mammals infected by β-lactamase producing bacteria.

The present invention provides the compounds of the formula (I):

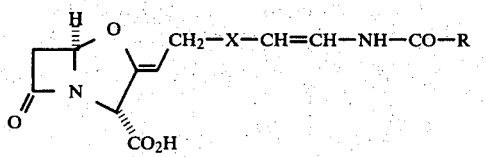

and pharmaceutically acceptable salts and in-vivo hydrolysable esters thereof wherein R is a hydrogen atom or an alkyl group of 1 to 6 carbon atoms and X is a sulphur atom or a SO or $SO_2$ group.

Suitably X in the compound of the formula (I) is a sulphur atom. Preferably X in the compound of the formula (I) is a $SO_2$ group.

A preferred value for R is the hydrogen atom. Suitably R is an alkyl group of 1 to 6 carbon atoms, for example R is a methyl, ethyl, n-propyl, isopropyl, n-butyl, t-butyl, sec-butyl, or isobutyl group. From these groups preferred values for R include the methyl and ethyl groups.

In the compounds of the formula (I) the double bond between the —X— and —NH— groups may be in either the E- or Z-configuration, but the E-configuration, is preferred.

From the foregoing it will be appreciated that preferred compounds of this invention are those of the formula (II):

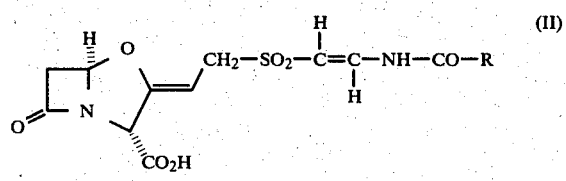

and their pharmaceutically acceptable salts and in-vivo hydrolysable esters.

A particularly preferred group of compounds of this invention is that of the formula (III):

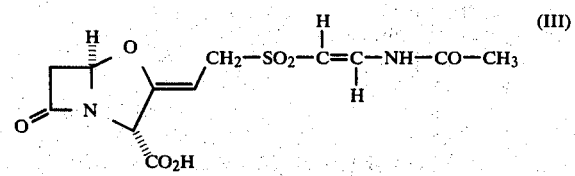

and its pharmaceutically acceptable salts and in-vivo hydrolysable esters.

The compounds of the formulae (I)–(III) are suitably provided in the form of the free acid.

The compounds of the formulae (I)–(III) are aptly in the form of a pharmaceutically acceptable salt.

Examples of pharmaceutically acceptable salts of the compounds of the formulae (I)–(III) include the alkali metal salts such as sodium or potassium, alkaline earth metal salts such as calcium or magnesium, and ammonium or substituted ammonium salts for example those with lower alkylamines such as triethylamine, hydroxy-lower alkylamines such as 2-hydroxyethylamine, bis-(2-hydroxyethyl)-amine, tris-(hydroxymethyl)amine or tris-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine or N,N'-bis-dehydroabietylethylenediamine.

Thus suitable salts of this invention include the sodium, potassium, calcium, magnesium and ammonium salts, of these the sodium, potassium, calcium and magnesium salts are favoured pharmaceutically acceptable salts.

The compounds of the formulae (I)–(III) may be provided as in-vivo hydrolysable esters. Such esters are those which hydrolyse in the human body to produce the parent acid. Suitable in-vivo hydrolysable esters include those esters known to give in-vivo hydrolysis in penicillins. Thus suitable esters include those of the sub-formula (a):

$$-CO-O-CHR_1-O-CO-R_2 \qquad (a)$$

wherein $R_1$ is a hydrogen atom, or a methyl or phenyl group; $R_2$ is an alkyl group of 1 to 6 carbon atoms, a phenyl group, an alkyl group of 1 to 3 carbon atoms substituted by a phenyl group, an alkoxy group of 1 to 6 carbon atoms, a phenoxyl group, or an alkoxyl group of 1 to 3 carbon atoms substituted by a phenyl group; or $R_1$ is attached to $R_2$ to form a 1,2-diphenylene or 4,5-dimethoxy-1,2-diphenylene group.

Favourably $R_1$ is hydrogen.

When $R_1$ is hydrogen suitably $R_2$ is selected from methyl, ethyl, n-propyl, iso-propyl, n-butyl, tert-butyl, phenyl, benzyl, methoxy, ethoxy, n-propyloxy and iso-propyloxy. Preferably $R_2$ is tert-butyl.

Favourably $R_1$ and $R_2$ are joined so that the ester is a phthalidyl or 3,4-dimethoxyphthalidyl ester.

Of these esters those favoured as in-vivo hydrolysable esters are the acetoxymethyl, acetoxyethyl, phthalidyl, ethoxycarbonyloxymethyl, α-ethoxycarbonyloxyethyl and pivaloyloxymethyl esters.

The in-vivo hydrolysable nature of the ester may be confirmed by administration to an animal such as a mouse or rat and determination of the presence of a compound of the formula (I) or a salt thereof in the blood or urine of the animal. Alternatively hydrolysis in human blood or serum may be determined.

It must be realised that salts of the compounds of the formulae (I)–(III) formed with pharmaceutically unacceptable ions are useful as they may serve as intermediates in the preparation of pharmaceutically acceptable salts by ion-exchange, or they may be useful as intermediates in the preparation of in-vivo hydrolysable esters. Examples of such salts are the lithium and tert-butylammonium salts. These are solid easily prepared and stored salts which may be converted into other salts such as sodium potassium, calcium, magnesium or like salt by ion-exchange.

The present invention also provides a pharmaceutical composition which comprises a compound of the formula (I) or a pharmaceutically acceptable salt or in-vivo hydrolysable ester thereof and a pharmaceutically acceptable carrier.

Most suitably the composition of this invention will contain a pharmaceutically acceptable salt of a compound of the formula (I). Favourably said salt is of the compound of the formula (III).

The compositions of this invention will generally contain from 25 mg to 500 mg of the compound of the invention but more usually from 50 mg to 250 mg of said compound, for example 75, 100, 125, 150, 175, 200 or 225 mg.

The compositions may be administered orally or by injection from 1 to 6 times a day and more usually from 2 to 4 times a day. The usual daily dose for a 70 kg adult human will be in the range 80 mg to 800 mgs and more usually from 125 mg to 500 mg.

Since the compounds of this invention have a degree of antibacterial activity in their own right they may be used to treat infections due to strains of *Staphylococcus aureus, Escherichia coli, Klebsiella aerogenes,* Proteus spp. for example they may be used to treat urinary tract infections due to such organisms or mastitis in cattle due to such organisms.

However as has previously indicated it is believed that the greatest usefulness of the compounds of the formula (I) and their pharmaceutically acceptable salts and in-vivo hydrolysable esters lies in their ability to inactivate bacterial β-lactamase and so enhance the in-vivo effectiveness of penicillins or cephalosporins. It is possible to administer the above described compositions to a mammal which is concurrently or consecutively also treated with a penicillin or cephalosporin. In this form of therapy the penicillin or cephalosporin is used in its conventional dosage. However for greater convenience and better control it is preferred to include the penicillin or cephalosporin in the same unit dose composition as the compound of the formula (I) or its pharmaceutically acceptable salt or in-vivo hydrolysable ester.

Accordingly in a further aspect this invention provides a pharmaceutical composition which comprises a penicillin or cephalosporin, a compound of the formula (I) or a pharmaceutically acceptable salt or in-vivo hydrolysable ester thereof and a pharmaceutically acceptable carrier.

When used herein the term "penicillin" extends to the penicillin itself and to its pharmaceutically acceptable salts and pro-drugs. Similarly when used herein the term "cephalosporin" extends to the cephalosporin itself and to its pharmaceutically acceptable salts and pro-drugs.

The synergistic composition may be adapted for oral or parenteral administration except of course if the penicillin or cephalosporin included is not one orally administrable when the synergistic composition will be adapted for parenteral administration.

British Patent Specifications Nos. 1508977 and 1508978 disclose suitable forms of synergistic composition and are incorporated herein by reference. By replacing the clavulanic acid or its salt or ester of said specifications by the compound of the formula (I) or its pharmaceutically acceptable salt or in-vivo hydrolysable ester, the desired composition of this invention results.

Particularly favoured orally administrable synergistic compositions of this invention are those which comprise amoxycillin trihydrate equivalent to 100 mg to 1000 mg of amoxycillin, the compound of the formula (III) or a pharmaceutically acceptable salt thereof equivalent to 50 mg to 500 mg of the compound of the formula (III).

Most suitably this composition will contain amoxycillin trihydrate equivalent to 200 mg to 600 mg of amoxycillin. Most suitably this composition will contain a pharmaceutically acceptable salt of the compound of the formula (III) equivalent to 100 mg to 300 mgs of the compound of the formula (III).

The present invention also provides a process for the preparation of a compound of the formula (I) as hereinbefore defined or a pharmaceutically acceptable salt or in-vivo hydrolysable ester thereof which process comprises the reaction of a cleavable ester of a compound of the formula (IV):

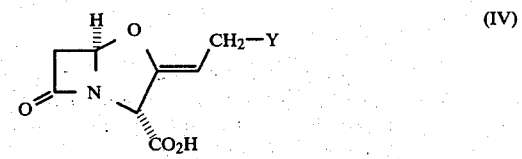

wherein Y is a displaceable atom or group, with a thiolate of a thiol of the formula (V):

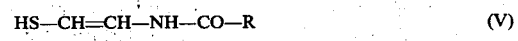

wherein R is as defined in relation to formula (I), to yield the cleavable ester of the compound of the formula (I) wherein X is a sulphur atom and thereafter optionally performing one or more of the following steps:

(a) oxidising the sulphur atom to a SO or SO₂ group,
(b) cleaving the cleavable ester to yield the compound of the formula (I) or salt thereof,
(c) converting the compound of the formula (I) or salt thereof into its pharmaceutically acceptable salt or in-vivo hydrolysable ester,
(d) converting a salt of the compound of the formula (I) into its free acid,
(e) isomerising the double bond of the side-chain.

When used herein the term "cleavable ester" means an ester cleavable by chemical methods such as hydrogenolysis, dissolving metal reduction or mild base hydrolysis, or an ester hydrolysable in-vivo to a compound of the formula (I) or its salt.

Suitable moieties Y displaceable by the thiolate include conventional displaceable groups such as sulphonate or carboxylate esters such as $OSO_2R^1$, $OCOR^1$ or $OCO_2R^1$ where $R^1$ is an inert organic group such as a lower alkyl group (such as a methyl, ethyl, propyl or butyl group) optionally substituted by one or more halogen atoms, a phenyl, benzyl, methoxyphenyl, methylphenyl, halophenyl, nitrophenyl or like group.

Other suitable moieties Y displaceable by the thiolate are halogen atoms, for example a chlorine or bromine atom.

Preferred values of Y are a chlorine or bromine atom, or a dichloroacetoxy, mesyloxy, tosyloxy or phenylsulphonyloxy group. Particularly preferred values of Y are chlorine and dichloroacetoxy.

The thioetherification reaction may be carried out at a non-extreme temperature such as −60° C. to +60° C., preferably from −30° C. to +30° C. The thioetherification reaction may be performed in an inert non-hydroxylic solvent such as dimethylformamide.

Suitable chemically cleavable esters of the compounds of the formulae (I) and (IV) include those of the sub-formulae (a) and (b):

----CO$_2$A$^1$            (a)

----CO$_2$CHA$^2$A$^3$     (b)

wherein A$^1$ is an alkyl group of 1–6 carbon atoms optionally substituted by a hydroxy group or an alkoxy group of 1–4 carbon atoms; A$^2$ is an alkenyl group of up to 5 carbon atoms or is a phenyl group optionally substituted by a fluorine, chlorine or bromine atom, or a nitro or alkyl or alkoxyl group of up to 4 carbon atoms; and A$^3$ is a hydrogen atom, an alkyl group of up to 4 carbon atoms or a phenyl group optionally substituted by a fluorine, chlorine or bromine atom, or a nitro or alkyl or alkoxy group of up to 4 carbon atoms.

Cleaving the cleavable ester of the compound of the formula (I) to form the parent acid or its salt may be achieved by hydrogenolysis, dissolving metal reduction or hydrolysis. Thus for example an ester such as a methyl, ethyl, methoxymethyl, ethoxymethyl or acetoxymethyl ester may be subjected to mild base hydrolysis to yield a salt of a compound of the formula (I). Suitably these esters may be hydrolysed by maintaining the pH of the medium at 7.5 to 10 until the hydrolysis is effected. Most suitably a readily hydrolysable ester such as the methoxymethyl ester is employed in this process. The pH may be maintained in the desired range in a pH-stat by the addition of a solution or suspension of a base such as LiOH, NaOH, KOH, Ca(OH)$_2$, Mg(OH)$_2$, or the like at a rate that prevents the accumulation of excess base which would cause the pH to increase unacceptably.

Dissolving metal reduction may be carried out using iron/ammonium chloride systems; but is not favoured for sulphoxides.

Suitable methods of hydrogenolysis of esters of the compounds of formula (I) include hydrogenation in the presence of a transition metal catalyst. Suitable hydrogenolysable esters of the compound of the formula (I) include those where the ester moiety is of the sub-formula CO$_2$CHA$^2$A$^3$ as hereinbefore defined and of these the benzyl and p-methoxybenzyl esters are particularly suitable. The p-nitrobenzyl ester is a preferred ester.

The pressure of hydrogen used in the reaction may be low, medium or high, but in general an approximately atmospheric or slightly superatmospheric pressure of hydrogen is preferred. The transition metal catalyst employed is preferably palladium, for example palladium on charcoal, palladium on barium sulphate, palladium on calcium carbonate or the like. The hydrogenation may be effected in any convenient solvent in which the ester is soluble such as tetrahydrofuran, ethyl acetate, ethanol, aqueous ethanol or the like. If this hydrogenation is carried out in the presence of a base then a salt of the compound of formula (I) is produced. Suitable bases for inclusion include NaHCO$_3$, Na$_2$CO$_3$, K$_2$CO$_3$, CaCO$_3$, MgCO$_3$, Li$_2$CO$_3$ and the like. If no base is present then hydrogenation leads to the preparation of an acid of formula (I) which may then be neutralised if desired to yield a salt. Suitable bases for such neutralisation include LiOH, NaHCO$_3$, KOH, Ca(OH)$_2$, Ba(OH)$_2$, Mg(OH)$_2$, NH$_4$OH, N(C$_2$H$_5$)$_3$, Na ethylhexanoate, K ethylhexanoate and the like e.g. MgO and NH$_2$C(CH$_3$)$_3$.

The lithium salts of the compounds of formula (I) tend to be more easily prepared in pure crystalline form than other salts of the compounds of formula (I). It is therefore often convenient to first form the lithium salt and then convert this into a further salt by ion-exchange, for example by passing a solution of the lithium salt through a bed of cation exchange resin in sodium, potassium, calcium, ammonium or like form. Suitable cation exchange resins include Amberlite IR 120 and equivalent resins. Another salt suitable for use as an intermediate in this way is the t-butylamine salt.

Oxidation of a compound of the formula (I) or a salt or cleavable ester thereof wherein X is a sulfur atom may be effected by reaction with an organic per acid such as peracetic acid, metaperiodic acid and m-chloroperbenzoic acid. Normally one equivalent of the acid is used for oxidation to the sulfoxide level whereas two or more equivalents are used for oxidation to the sulfone level. The reaction is generally carried out at a depressed temperature which may conveniently be at about 0°. Suitable solvents are inert organic solvents such as dichloromethane and chloroform.

The side chain of the compounds of this invention may be isomerised if desired, for example by treatment with mercuric chloride in tetrahydrofuran at room temperature.

The compounds of this invention may be purified by conventional procedures such as crystallisation, recrystallisation, chromatography and the like.

The following Examples illustrate the invention.

EXAMPLE 1 p-Nitrobenzyl 9-Z-(2′-acetamidovinylthio)-9-deoxy clavulanate

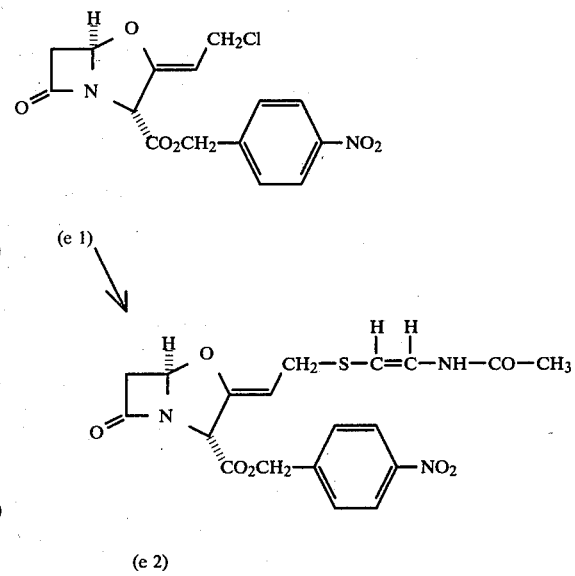

Sodium Z-2-acetamidovinylthiolate (0.35 g, 1.77 mmole as a 1:1 mixture with sodium chloride) was added to a stirred, ice cooled solution of p-nitrobenzyl 9-chloro-9-deoxyclavulanate (e 1) (0.63 g, 1.78 mmole) in dry DMF (20 ml) and stirring continued for 30 mins.

Ethyl acetate (100 ml) was added and the mixture washed with water (2×100 ml), dried over MgSO$_4$ and evaporated. The residue was chromatographed on silica (35 g, Merck Keisel gel 60, 230–400 mesh) in a 3 cm diameter column under slight air pressure, eluting with ethyl acetate/petrol (45% ethyl acetate). The title compound was detected on tlc (silica, eluent ethyl acetate/petrol 2:1) at r.f. 0.55 by observation of the phase under UV (254 nm) and by spraying the plates with dilute potassium permanganate solution. Appropriate fractions were combined and evaporated under reduced pressure to provide p-nitrobenzyl 9-Z-(2'-acetamidovinylthio)-9-deoxyclavulanate (e 2) (0.40 g, 52%) as a yellow foam. $[\alpha]_D^{20} -19.2°$ (c0.8; CHl$_3$); $\nu_{max}$ (CHCl$_3$) 3430, 1808, 1760, 1692 and 1627 cm$^{-1}$; $\nu_{max}$ (dioxan) 266.5 nm (17800); $\delta$(CDCl$_3$) 2.07 (3H, s, —COC$\underline{H}_3$), 3.05 (1H, d, J 17 Hz, 6β-C$\underline{H}$), 3.32 (2H, d, J 8 Hz, 9-C$\underline{H}_2$), 3.51 (1H, dd, J 17 and 2.5 Hz, 6α-C$\underline{H}$), 4.72 (1h, dt, J 8 and 1 Hz, 8-C$\underline{H}$), 5.0–5.4 (4H, m, 3-C$\underline{H}$, —SC$\underline{H}$= and —C$\underline{H}_2$Ar), 5.68 (1H, d, J 2.5 Hz, 5-C$\underline{H}$), 7.04 (1H, dd, J 11.5 and 8 Hz, —NHC$\underline{H}$=), 7.4–7.8 (3H, m, with 2 proton d at 7.51, NH and 2 Ar-H), 8.21 (2H, d, 2 Ar-H).

EXAMPLE 2

Lithium 9-Z-(2'-acetamidovinylthio)-9-deoxyclavulanate

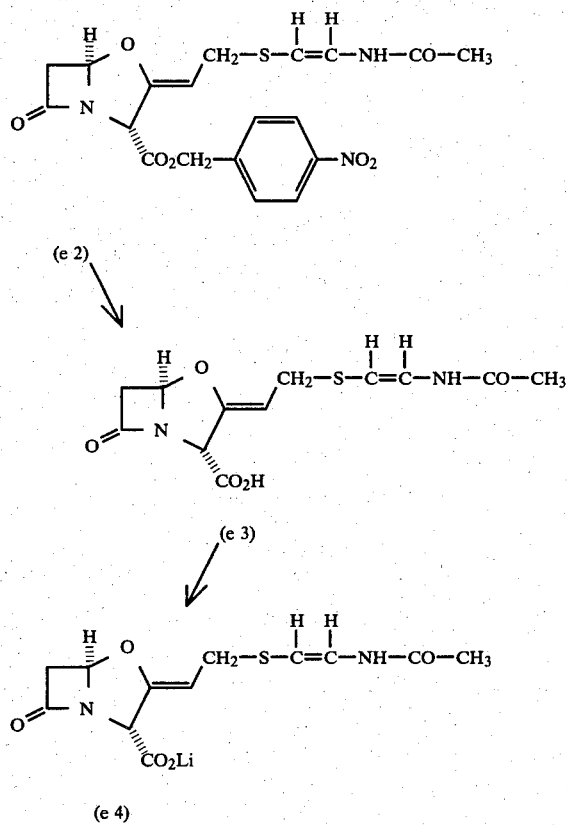

(e 4)

p-Nitrobenzyl 9-Z-(2'-acetamidovinylthio)-9-deoxy clavulanate (e 2) (0.143 g, 0.33 mmole) was dissolved in tetrahydrofuran (4 ml) with stirring, ice cooled and treated with 1 M aqueous ammonium chloride solution (4 ml) and iron powder (0.5 g). After 20 mins. a further 0.3 ml of 1 M aqueous ammonium chloride solution and 0.5 g iron powder were added and stirring continued for 45 mins. 20 ml ethyl acetate was added and H$_2$S bubbled through the mixture for 10 mins with ice cooling. The mixture was filtered through celite and the residues washed with 20 ml water. The aqueous layer of the filtrate (including washings) was saturated with NaCl, acidified with 1 N aqueous hydrochloric acid to pH 2.5 and separated from the organic layer. The aqueous layer was further extracted with ethyl acetate (2×20 ml) and the combined ethyl acetate extracts dried over MgSO$_4$. After filtration the ethyl acetate was extracted with pH 7 phosphate buffer (3×20 ml.). The combined aqueous extracts were saturated with NaCl, acidified to pH 2.5 with 1 N aqueous hydrochloric acid and extracted with ethyl acetate (3×20 ml.). The ethyl acetate extracts were dried over MgSO$_4$ and evaporated and the residue quickly taken up in tetrahydrofuran (10 ml) and water (10 ml) to yield a solution of 9-Z-(2-acetamidovinylthio)-9-deoxyclavulanic acid (e 3). This solution was brought to pH 7 by addition of 0.1 N aqueous lithium carbonate solution, washed with ether (10 ml) and freeze dried. Lithium 9-Z-(2'-acetamidovinylthio)-9-deoxyclavulanate (e 4) was obtained as a pale yellow solid (0.054 g, 54%). $[\alpha]_D^{20} +49.5°$ (c. 0.7; H$_2$O); $\nu_{max}$ (KBr) 1780, 1670(s), 1620 cm$^{-1}$; $\nu_{max}$ (H$_2$O) 224 nm (10210) and 268 nm (9010); $\delta$(D$_2$O-HOD=4.61) 2.10 (3H, s, —COC$\underline{H}_3$), 3.06 (1H, d, J 17.5 Hz, 6β-C$\underline{H}$), 3.2–3.7 (3H, m, 6α-CH and 9-C$\underline{H}_2$), 4.5–5.1 (2H, m, partially obscured by HOD, 3-C$\underline{H}$ and 8-C$\underline{H}$), 5.50 (1H, d, J 8 Hz, —SC$\underline{H}$=), 5.68 (1H, d, J 2.5 Hz, 5-C$\underline{H}$), 6.86 (1H, d, J 8 Hz, =C$\underline{H}$NH—).

EXAMPLE 3 p-Nitrobenzyl 9-Z-(2'-acetamidovinylsulfinyl)-9-deoxy clavulanate

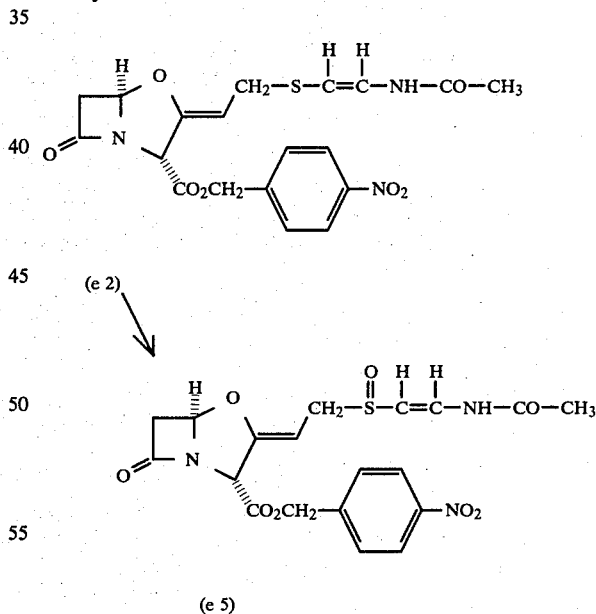

(e 5)

p-Nitrobenzyl 9-Z-(2'-acetamidovinylthio)-9-deoxy clavulanate (e 2) (0.25 g, 0.577 mmole) was dissolved in dichloromethane (20 ml), ice cooled with stirring and treated dropwise over 5 mins. with a solution of m-chloroperbenzoic acid (0.10 g, 0.58 mmole) in dichloromethane (5 ml). After stirring for 30 mins. the solution was washed with 1 N aqueous sodium bicarbonate (2×20 ml) and water (20 ml), dried over MgSO$_4$ and evaporated. The residue was chromatographed on silica (30 g) in a similar manner to example 1, eluting with ethyl acetate to provide p-nitrobenzyl 9-Z-(2'-acetamidovinylsulfonyl)-9-deoxyclavulanate (e 5) (0.12 g, 46%), [α]$_D^{20}$−12.2° (c. 0.9; CHCl$_3$); ν$_{max}$ (CHCl$_3$) 3300, 1810, 1758, 1705(s), 1692 and 1630 cm$^{-1}$, ν$_{max}$ (dioxan) 268 nm (19320); δ(CDCl$_3$) 2.05 (3H, s, —COC$\underline{H}_3$), 3.08 and 3.11 (1H, 2d, J 17 Hz, 6β-C$\underline{H}$), 3.4–4.0 (3H, m, 6α-C$\underline{H}$ and 9-C$\underline{H}_2$), 4.7–5.1 (2H, m, 8-C$\underline{H}$ and —SOC$\underline{H}$=), 5.20 (1H, s, 3-C$\underline{H}$), 5.27 (2H, s, —C$\underline{H}_2$Ar), 5.73 (1H, d, J 2.5 Hz, 5-C$\underline{H}$), 7.3–7.6 (3H, m, 2 Ar-H and =C$\underline{H}$NH—), 8.22 (2H, d, 2 Ar-H), 10.30 (1H, d, J 11 Hz, N$\underline{H}$).

EXAMPLE 4

Lithium 9-Z-(2'-acetamidovinylsulfinyl)-9-deoxyclavulanate

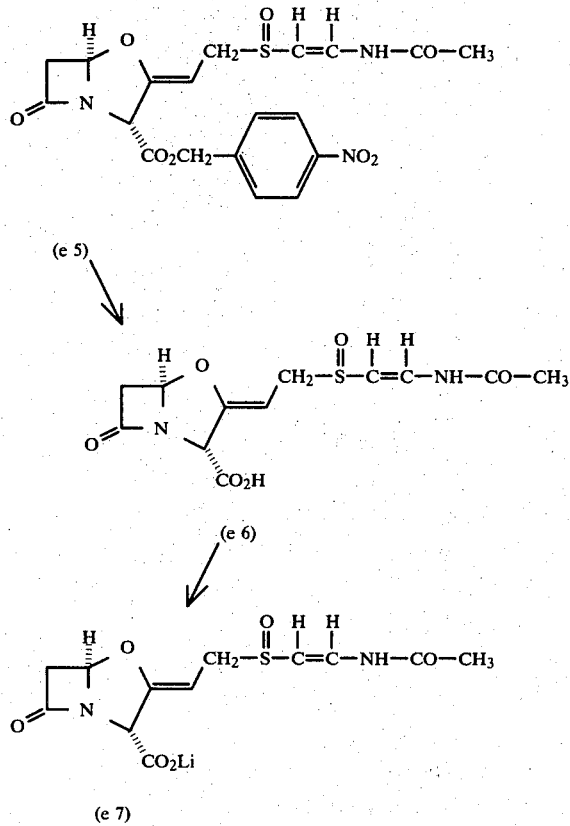

A solution of p-nitrobenzyl 9-Z-(2'-acetamidovinylsulfinyl)-9-deoxyclavulanate (e 5) (0.138 g, 0.307 mmole) in tetrahydrofuran (50 ml) was added to a prehydrogenated suspension of 10% palladium/charcoal (0.20 g) in tetrahydrofuran (50 ml). Hydrogenation at one atmosphere was continued for 2 hours, the suspension filtered through celite and the filtrate evaporated to 5 ml. At this point the solution contained 9-Z-(2'-acetamidovinylsulfinyl)-9-deoxyclavulanic acid (e 6). Water (20 ml) was added, followed by a solution of 0.1 M aqueous lithium carbonate (1.53 ml). The solution was ether lithium carbonate (1.53 ml). The solution was ether washed (3×20 ml), adjusted to pH 7 with 0.5 N aqueous hydrochloric acid and freeze dried to provide lithium 9-Z-(2'-acetamidovinylsulfinyl)-9-deoxyclavulanate (e 7) (0.07 g, 71%) as a yellow solid. [α]$_D^{20}$+36.8° (c. 0.8; DMSO); ν$_{max}$ (KBr) 1783, 1685 and 1620 cm$^{-1}$; λ$_{max}$ (H$_2$O) 236 nm (10400); δ(D$_2$O-HOD=4.61), 2.06 (3H, s, —COC$\underline{H}_3$), 3.04 (1H, d, J 17.5 Hz, 6β-C$\underline{H}$), 3.52 (1H, dd, J 17.5 and 2.5 Hz, 6α-CH), 3.75 (2H, broad d, J 8 Hz, 9-CH$_2$), 5.55 (1H, d, J 8 Hz, —SOC$\underline{H}$=), 5.69 (1H, broad s, 5-C$\underline{H}$). 7.34 (1H, d, J 8 Hz, =C$\underline{H}$NH—), 8-C$\underline{H}$ and 3-C$\underline{H}$ obscured by HOD.

EXAMPLE 5 p-Nitrobenzyl 9-Z-(2'-acetamidovinylsulfonyl)-9-deoxyclalvulanate

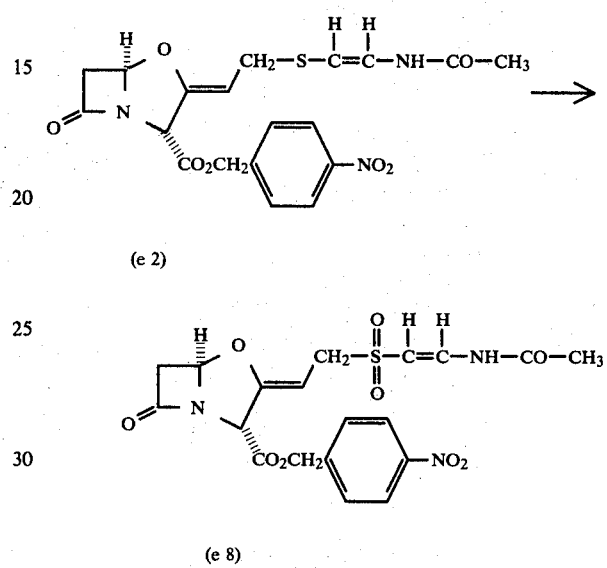

A stirred, ice cooled solution of p-nitrobenzyl 9-Z-(2'-acetamidovinylthio)-9-deoxyclavulanate (e 2) (0.60 g, 1.38 mmole) in dichloromethane (50 ml) was treated dropwise over 10 mins. with a solution of m-chloroperbenzoic acid (0.50 g, 2.90 mmole). The mixture was stirred at 0°–5° C. for 2 hrs, washed with 1 N aqueous sodium bicarbonate solution (2×50 ml) and water (50 ml), dried over MgSO$_4$ and evaporated. The residue was chromatographed on silica (30 g) in a similar manner to that of Example 1, eluting with ethyl acetate/petrol 1:1. p-Nitrobenzyl 9-Z-(2'-acetamidovinylsulfonyl)-9-deoxyclavulanate (e8) thus obtained crystallised from chloroform/petrol (0.39 g, 60%) as a white microcrystalline solid, m.p. 138°–40° C. [α]$_D^{20}$−8.9° (c. 0.9; CHCl$_3$); found: C, 49.0; H, 4.4; N, 9.0; S, 6.9% C$_{19}$H$_{19}$N$_3$O$_9$S requires C, 49.0; H, 4.1; N, 9.0; S, 6.9% ν$_{max}$ (CHCl$_3$) 3380, 1810, 1758, 1722, 1698 (s) and 1629 cm$^{-1}$; λ$_{max}$ (dioxan) 257 nm (22580); δ(DMSO-d$_6$) 2.09 (3H, s, COCH$_3$), 3.10 (1H, d, J 17 Hz, 6β-C$\underline{H}$), 3.67 (1H, dd, J 17 and 3 Hz, 6α-C$\underline{H}$), 3.94 (2H, d, J 8 Hz, 9-C$\underline{H}_2$), 4.78 (1H, t, J 8 Hz, 8-CH), 5.33 (2H, s, —C$\underline{H}_2$ Ar), 5.45 (1H, d, J 9.5 Hz, —SO$_2$C$\underline{H}$=), 5.54 (1H, s, 3-C$\underline{H}$), 5.77 (1H, d, J 3 Hz 5-C$\underline{H}$), 7.45 (1H, dd, J 12 and 9.5 Hz, =CHN$\underline{H}$—), 7.64 and 8.23 (4H, 2d, Ar-H), 9.67 (1H, d, J 12 Hz, NH).

EXAMPLE 6

Lithium 9-Z-(2'-acetamidovinylsulfonyl)-9-deoxyclavulanate

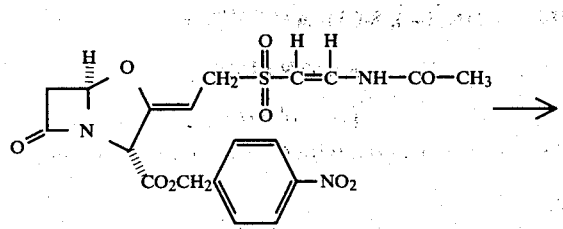

(e 8)

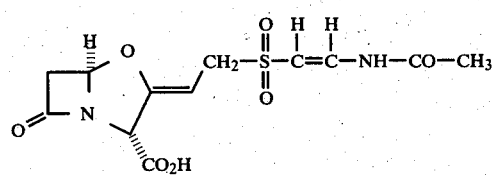

(e 9)

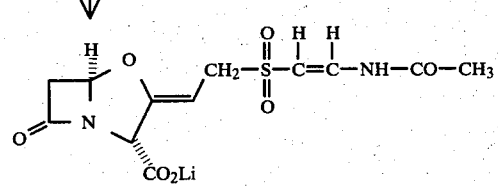

(e 10)

p-Nitrobenzyl 9-Z-(2'-acetamidovinylsulfonyl)-9-deoxy clavulanate (e8) (0.30 g. 0.645 mmole) was dissolved in tetrahydrofuran (15 ml) with stirring, ice cooled and treated with 1 M aqueous ammonium chloride solution (15 ml) and iron powder (1.1 g). After 20 mins. a further 5 ml of 1 M aqueous ammonium chloride solution and 1.1 g iron powder were added and stirring continued for 45 mins. 50 ml ethyl acetate was added and H$_2$S bubbled through the mixture for 10 mins. with ice cooling. The mixture was filtered through celite and the residues washed with 30 ml water. The aqueous layer of the filtrate (including washings) was saturated with NaCl, acidified with 1 N aqueous hydrochloric acid to pH 2.5 and separated from the organic layer. The aqueous was further extracted with ethyl acetate (2×30 ml) and the combined ethyl acetate extracts dried over MgSO$_4$. After filtration the ethyl acetate was extracted with pH 7 phosphate buffer (3×20 ml). The combined aqueous extracts were saturated with NaCl, acidified to pH 2.5 with 1 N aqueous hydrochloric acid and extracted with ethyl acetate (3×20 ml). The ethyl acetate extracts were dried over MgSO$_4$ and evaporated and the residue quickly taken up in tetrahydrofuran (10 ml) and water (10 ml) to yield a solution of 9-Z-(2'-acetamidovinylsulfonyl)-9-deoxyclavulanic acid (e9). This solution was brought to pH 7 by addition of 0.1 N aqueous lithium carbonate solution, washed with ether (10 ml) and freeze dried. Lithium 9-Z-(2'-acetamidovinylsulfonyl)-9-deoxyclavulanate (e10) was obtained as a pale yellow solid (0.175 g, 80%).

$[\alpha]_D^{20}$+78.0° (c. 1.23; H$_2$O); $\nu_{max}$ (KBr) 1780, 1690, 1635 (s), 1615 cm$^{-1}$; $\lambda_{max}$ (H$_2$O) 227 nm (s) (13840) and 249 nm (20160); δ(D$_2$O-HOD=4.61) 2.17 (3H, s, —COC$\underline{H}_3$), 3.05 (1H, d, J 17 Hz, 6β-C$\underline{H}$, 3.56 (1H, dd, J 17 and 2.5 Hz, 6α-C$\underline{H}$), 4.01 (2H, AB of ABX, J 14 and 8 Hz, 9-C$\underline{H}_2$), 4.78 (1H, dt, J 8 and 1 Hz, 8-C$\underline{H}$), 4.93 (1H, br.s, 3-C$\underline{H}$), 5.53 (1H, d, J 9.5 Hz, —SO$_2$C$\underline{H}$=), 5.72 (1H, d, J 2.5 Hz, 5-C$\underline{H}$), 7.55 (1H, d, J 9.5 Hz, =C$\underline{H}$NH).

EXAMPLE 7 p-Nitrobenzyl 9-E-(2'-acetamidovinylthio)-9-deoxyclavulanate

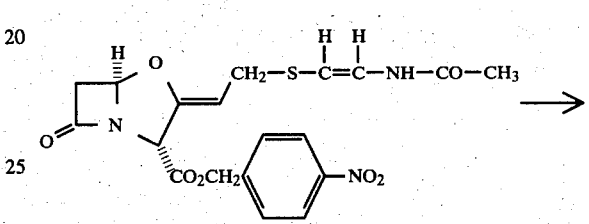

(e 2)

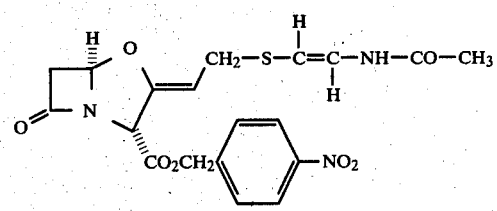

(e 11)

p-Nitrobenzyl 9-Z-(2'-acetamidovinylthio)-9-deoxyclavulanate (e 2) (1.0 g, 2.31 mmole) was dissolved in tetrahydrofuran (10 ml) and treated with mercuric chloride (0.15 g). The solution was stirred one hour at room temperature, evaporated and the residue chromatographed on silica (50 g), in a similar manner to that of Example 1, eluting with ethyl acetate/petrol 7:3 to provide p-nitrobenzyl 9-E-(2'-acetamido vinylthio)-9-deoxyclavulanate (e 11) (0.25 g, 25%) as a yellow foam. $[\alpha]_D^{20}$−19.2° (c. 1.3; CHCl$_3$); $\nu_{max}$ (CHCl$_3$) 3460, 1807, 1758, 1695 and 1623 cm$^{-1}$; $\lambda_{max}$ (ETOH) 240 nm (S) (13800) and 269 nm (17400); δ(CDCl$_3$) 1.97 (3H, s, —COC$\underline{H}_3$), 3.07 (1H, d, J 17 Hz, 6β-C$\underline{H}$), 3.27 (2H, d, J 8 Hz, 9-C$\underline{H}_2$), 3.49 (1H, dd, J 17 and 2.5 Hz, 6α-C$\underline{H}$), 4.71 (1H, broad t, J 8 Hz, 8-C$\underline{H}$), 5.11 (1H, broad s, 3-C$\underline{H}$), 5.29 (2H, s, —C$\underline{H}_2$Ar), 5.5–5.8 (2H, m, 5-C$\underline{H}$ and —SC$\underline{H}$=), 6.97 (1H, dd, J 14 and 10 Hz, =C$\underline{H}$NH—), 7.53 and 8.21 (4H, 2d, Ar-H), 8.57 (1H, d, J 10 Hz, NH); Found 433.0949 (M+); C$_{19}$H$_{19}$N$_3$O$_7$S requires 433.0958.

EXAMPLE 8

Lithium 9-E-(2′-acetamidovinylthio)-9-deoxyclavulanate

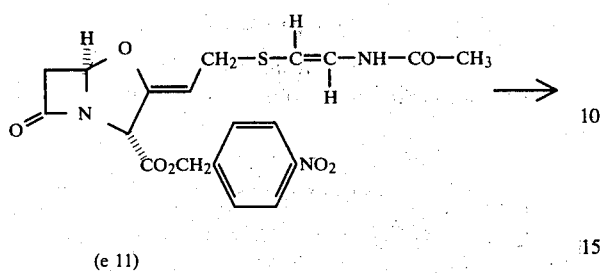

(e 11)

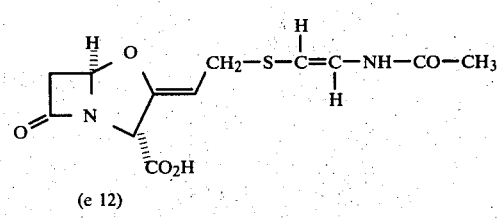

(e 12)

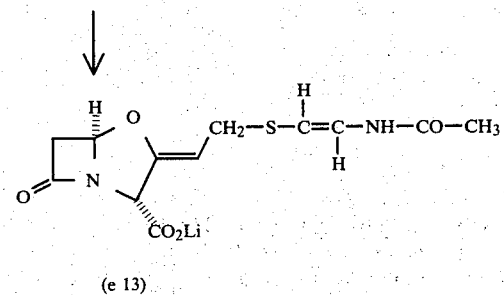

(e 13)

p-Nitrobenzyl 9-E-(2′-acetamidovinylthio)-9-deoxy clavulanate (e 11) (0.26 g, 0.60 mmole) was deprotected in an identical manner to that of Example 6, using the same reagent and solvent quantities to provide lithium 9-E-(2′-acetamidovinylthio)-9-deoxyclavulanate (e 13) (0.12 g, 66%) as a pale yellow solid. $[\alpha]_D^{20}+193.4°$ (c. 1.1; $H_2O$); $\nu_{max}$ (KBr) 1765, 1687, 1680 (s) and 1620 cm$^{-1}$; $\lambda_{max}$ ($H_2O$) 224 nm (13650) and 271 nm (10770); $\delta(D_2O\text{-HOD}=4.61)$ 1.97 (3H, s, —$COC\underline{H}_3$), 2.97 (1H, d, J 17 Hz, 6β-$C\underline{H}$), 3.1–3.7 (3H, m, 6α-CH and 9-$C\underline{H}_2$), 4.72 (1H, t, J 8 Hz, 8-$C\underline{H}$), 4.86 (1H, s, 3-CH), 5.62 (1H, d, J 2.5 Hz, 5-$C\underline{H}$), 5.74 (1H, d, J 14 Hz, —$SC\underline{H}$=), 6.79 (1H, d, J 14 Hz, =$C\underline{H}$NH—).

EXAMPLE 9 p-Nitrobenzyl 9-E-(2′-acetamidovinylsulfinyl)-9-deoxy clavulanate

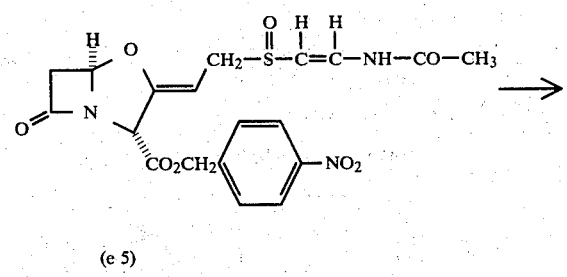

(e 5)

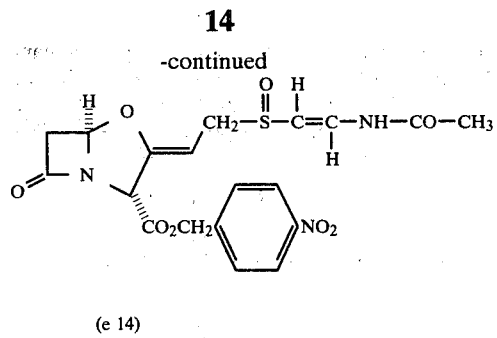

(e 14)

p-Nitrobenzyl 9-Z-(2′-acetamidovinylsulfinyl)-9-deoxyclavulanate (e 5) (0.25 g, 0.556 mmole) was dissolved in tetrahydrofuran (10 ml) at room temperature and mercuric chloride (0.027 g, 0.1 mmole) added. The solution was stirred for 2 hours and evaporated at reduced pressure. The residue was chromatographed on silica (30 g) in the manner of Example 1, eluting with ethyl acetate/ethanol 4:1 to provide p-nitro benzyl 9-E-(2′-acetamidovinylsulfinyl)-9-deoxyclavulanate (e 14) (0.18 g, 73%), as a white foam. $[\alpha]_D^{20}-5.7°$ (c. 1.2; CHCl$_3$); $\nu_{max}$ (CHCl$_3$) 3450(s), 3250(s), 1810, 1758, 1712 and 1630 cm$^{-1}$; $\lambda_{max}$ (EtOH) 255 nm (23760); $\delta$(CDCl$_3$) 2.04 (3H, s, —$COC\underline{H}_3$), 3.11 and 3.14 (1H, 2d, J 17 Hz, 6β-$C\underline{H}$), 3.3–3.8 (3H, m, 6α-CH and 9-$C\underline{H}_2$), 4.68 (1H, broad t, J 8 Hz, 8-$C\underline{H}$), 5.18 (1H, broad s, 3-$C\underline{H}$), 5.26 (2H, s, —$C\underline{H}_2$Ar), 5.73 (1H, d, J 2 Hz, 5-CH), 6.06 and 6.09 (1H, 2d, J 16 Hz, —$SOC\underline{H}$=), 7.1–7.7 (3H, m, =$C\underline{H}$NH— and 2 Ar-H), 8.20 (2H, d, 2 Ar-H), 9.59 (1H, d, J 10.5 Hz, NH).

EXAMPLE 10 p-Nitrobenzyl 9-E-(2′-acetamidovinylsulfinyl)-9-deoxy clavulanate

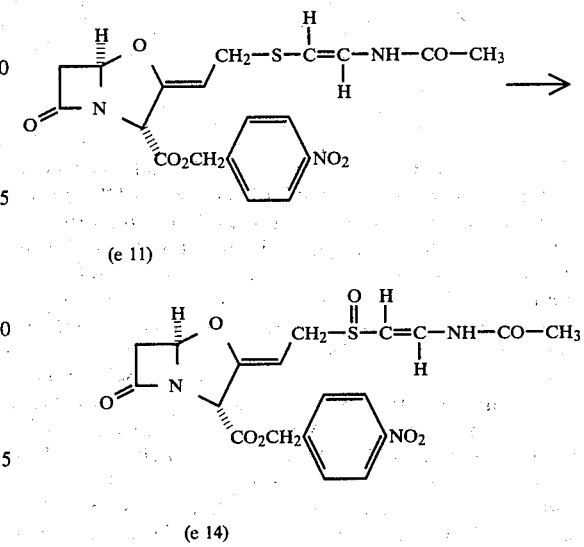

(e 11)

(e 14)

p-Nitrobenzyl 9-E-(2′-acetamidovinylthio)-9-deoxy clavulanate (e 11) (0.53 g, 1.22 mmole) was dissolved in dichloromethane (30 ml) with stirring and ice cooling and treated dropwise over 5 mins. with a solution of m-chloroperbenzoic acid (0.211 g, 1.22 mmole) in dichloromethane (10 ml). After stirring for 30 mins. at 0°–5° C. the solution was washed with 1 N aqueous sodium bicarbonate solution (2×30 ml) and water (30 ml), dried over MgSO$_4$ and evaporated. The residue was chromatographed on silica (30 g) in a manner similar to that of Example 1, eluting with ethyl acetate/ethanol 4:1 to provide p-nitrobenzyl 9-E-(2'-acetamido vinylsulfinyl)-9-deoxyclavulanate (e 14) (0.38 g, 69%), identical to the product of Example 9.

EXAMPLE 11

Lithium 9-E-(2'-acetamidovinylsulfinyl)-9-deoxyclavulanate

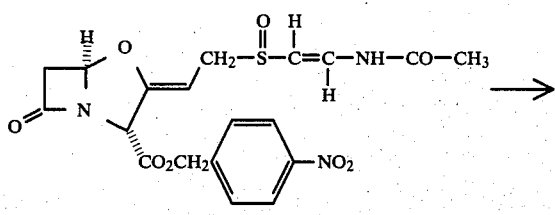

(e 14)

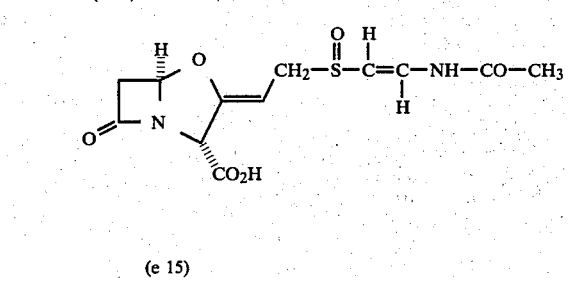

(e 15)

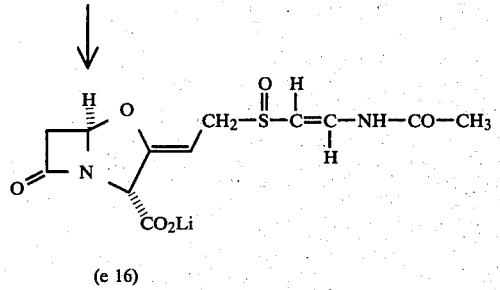

(e 16)

A solution of p-nitrobenzyl 9-E-(2'-acetamidovinylsulfinyl)-9-deoxyclavulanate (e14) (0.38 g 0.845 mmole) in tetrahydrofuran (50 ml) was added to a prehydrogenated suspension of 10% palladium/charcoal (0.60 g) in tetrahydrofuran (50 ml) and the mixture was hydrogenated at 1 atmosphere for 2½ hours and filtered through celite. The filtrate, which contained 9-E-(2'-acetamidovinylsulfinyl)-9-deoxyclavulanic acid (e15), was evaporated to 10 ml and treated dropwise over 5 mins with a solution of lithium carbonate (0.031 g 0.422 mmole) in water (30 ml). The mixture was washed with ethyl acetate (3×30 ml), acidified to pH 2 with 1 N aqueous hydrochloric acid, saturated with sodium chloride and extracted with ethyl acetate (3×30 ml). The combined extracts were dried over MgSO4 and evaporated, and the residue taken up immediately in tetrahydrofuran (5 ml). Water (10 ml) was added and the pH brought to 7 by dropwise addition of 0.1 M aqueous lithium carbonate solution. The resulting solution was washed with ether (10 ml) and freeze dried to provide lithium 9-E-(2'-acetamidovinylsulfinyl)-9-deoxyclavulanate (e16) (0.05 g, 18%) as a yellow solid. $[\alpha]_D^{20}+38.9°$ (c. 0.9; $H_2O$); $\nu_{max}$ (KBr) 1780, 1685 and 1620 $cm^{-1}$; $\lambda_{max}$ ($H_2O$) 234 nm (9910) and 245 nm (s) (9720); $\delta$($D_2O$-HOD=4.61) 2.07 (3H, s, —$COCH_3$), 3.01 (1H, broad d, J 17 Hz, 6β-C$\underline{H}$), 3.3–3.8 (3H, m, 6α-CH and 9-C$\underline{H_2}$), 4.91 (1H, broad s, 3-C$\underline{H}$), 5.67 (1H, broad s, 5-C$\underline{H}$), 6.08 (1H, d, J 14 Hz —SOC$\underline{H}$=), 7.33 and 7.38 (1H, 2d, J 14 Hz, =C$\underline{H}$NH—). 8-C$\underline{H}$ obscured by HOD.

EXAMPLE 12 p-Nitrobenzyl 9-E-(2'-acetamidovinylsulfonyl)-9-deoxyclavulanate

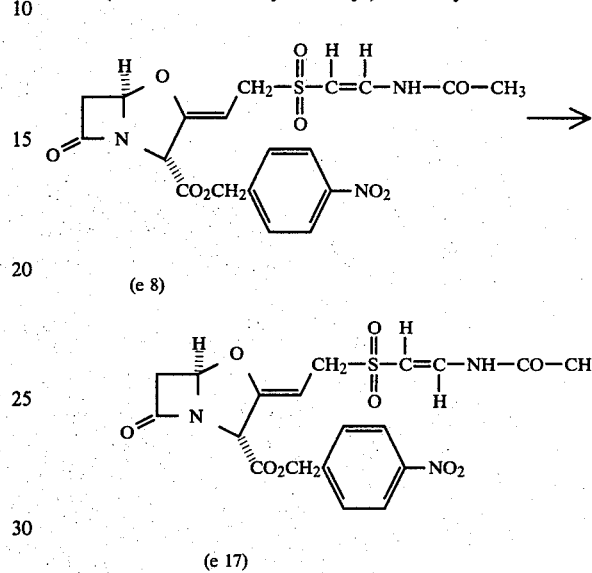

(e 8)

(e 17)

p-Nitrobenzyl 9-Z-(2'-acetamidovinylsulfonyl)-9-deoxy clavulanate (e 8) (0.40 g 0.86 mmole) was dissolved in tetrahydrofuran (20 ml) at room temperature and mercuric chloride (0.058 g 0.215 mmole) added. The solution was stirred for 3 hrs. and evaporated at reduced pressure. The residue was chromatographed on silica (30 g) in the manner of Example 1, eluting with ethyl acetate to provide p-nitrobenzyl 9-E-(2'-acetamidovinylsulfonyl)-9-deoxyclavulanate (e17) (0.30 g, 75%) as a white foam $[\alpha]_D^{20}-6.8°$ (c. 2.1; $CHCl_3$); $\nu_{max}$ ($CHCl_3$) 3300, 1810, 1758, 1730 and 1633 $cm^{-1}$; $\lambda_{max}$ (EtOH) 250 nm (22350); $\delta$($CDCl_3$) 2.11 (3H, s, —$COCH_3$), 3.07 (1H, d, J 17 Hz, 6β-C$\underline{H}$), 3.52 (1H, dd, J 17 and 2.5 Hz, 6α-C$\underline{H}$), 3.80 (2H, d, J 8 Hz, 9-C$\underline{H_2}$), 4.78 (1H, t, J 8 Hz, 8-C$\underline{H}$), 5.20 (1H, s, 3-C$\underline{H}$), 5.30 (2H, s, —$CH_2$Ar), 5.73 (1H, d, J 2.5 Hz, 5-C$\underline{H}$), 6.14 (1H, d, J 14 Hz, —$SO_2$C$\underline{H}$=), 7.4–7.8 (3H, m, =C$\underline{H}$NH— and 2 Ar-H), 8.21 (2H, d, 2 Ar-H), 8.61 (1H, d, J 10.5 Hz, NH).

EXAMPLE 13

Lithium 9-E-(2'-acetamidovinylsulfonyl)-9-deoxyclavulanate

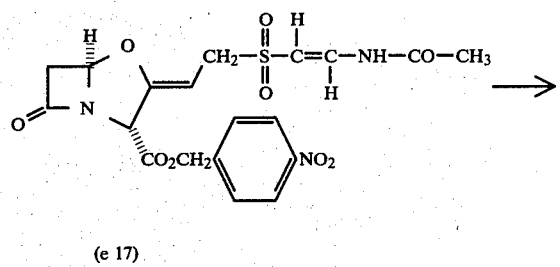

(e 17)

-continued

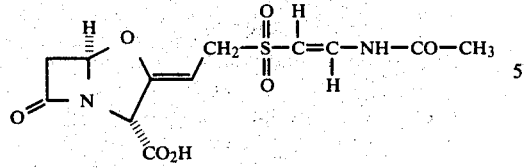

(e 18)

↓

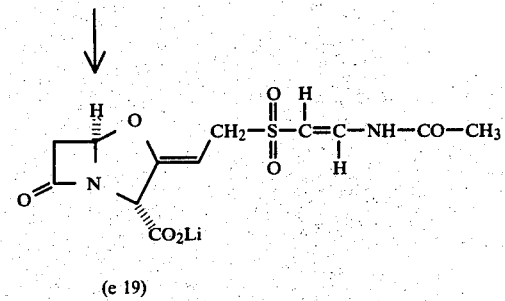

(e 19)

p-Nitrobenzyl 9-E-(2'-acetamidovinylsulfonyl)-9-deoxy clavulanate (e17) (0.28 g 0.60 mmole) was deprotected in an exactly identical manner to that of Example 6, using the same reagent and solvent quantities to provide lithium 9-E-(2'-acetamidovinylsulfonyl)-9-deoxyclavulanate (e19) (0.09 g, 45%) as a pale yellow solid. $[\alpha]_D^{20}+131.4°$ (c. 1.1; $H_2O$); $\nu_{max}$(KBr) 1780 (s), 1760, 1700, 1635 and 1615 cm$^{-1}$; $\lambda_{max}$($H_2O$) 247.5 nm (20630); $\delta$($D_2O$-HOD=4.61) 2.14 (3H, s, —COC$\underline{H}_3$), 3.01 (1H, d, J 17 Hz, 6$\beta$-CH), 3.58 (1H, dd, J 17 and 2.5 Hz, 6$\alpha$-C$\underline{H}$), 3.7–4.2 (2H, m, 9-C$\underline{H}_2$), 4.73 (1H, t, J 8 Hz, 8-CH), 4.96 (1H, s, 3-C$\underline{H}$), 5.70 (1H, d, J 2.5 Hz, 5-C$\underline{H}$) 6.11 (1H, d, J 14 Hz, —SO$_2$C$\underline{H}$), 7.54 (1H, d, J 14 Hz, =C$\underline{H}$NH).

EXAMPLE 14 p-Nitrobenzyl 9-Z-(2'-acetamidovinylthio)-9-deoxy clavulanate and p-nitrobenzyl 9-E-(2'-acetamidovinyl thio)-9-deoxyclavulanate

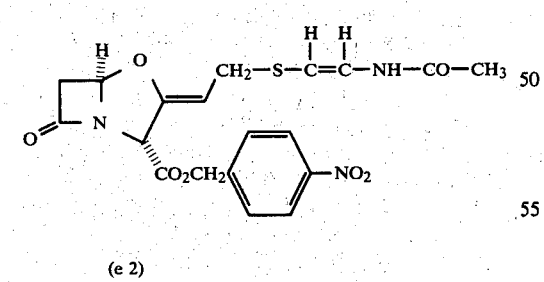

(e 2)

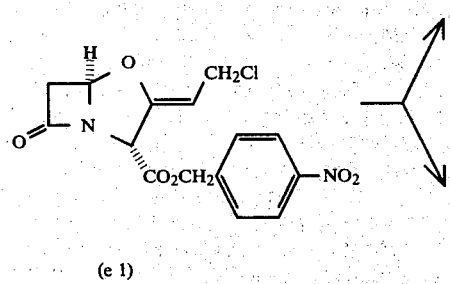

(e 1)

-continued

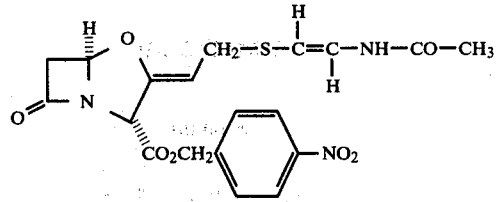

(e 11)

A 1:1 mixture of sodium Z-2-acetamidovinylthiolate and sodium E-2-acetamidovinylthiolate (4.15 g, 0.021 mole) was added to a stirred, ice cooled solution of p-nitrobenzyl-9-chloro-9-deoxyclavulanate (e 1) (6.78 g, 0.019 mole) in 200 ml dry dimethylformamide and stirring continued for 35 mins. Ethyl acetate (400 ml) was added and the mixture washed with water (3×300 ml), dried over MgSO$_4$ and evaporated. Chromatography of the residue on silica (100 g, in a 4 cm diameter column) in the manner of Example 1, eluting with ethyl acetate/petrol 6:4, provided p-nitro benzyl 9-Z-(2'-acetamidovinylthio)-9-deoxyclavulanate (e 2) (less polar, 1.33 g, 16%) and p-nitrobenzyl 9-E-(2'-acetamidovinylthio)-9-deoxyclavulanate (e 11) (more polar, 1.78 g, 21%). These products were identical to the products of Examples 1 and 7 respectively.

EXAMPLE 15 p-Nitrobenzyl 9-E-(2'-acetamidovinylsulfonyl)-9-deoxyclavulanate

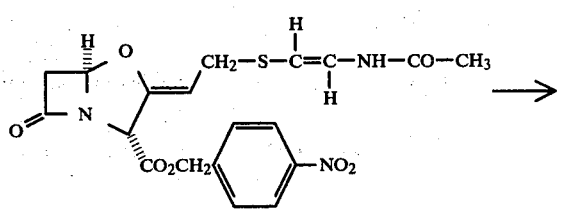

(e 11)

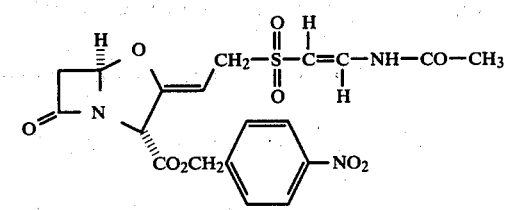

(e 17)

A stirred, ice cooled solution of p-nitrobenzyl 9-E-(2'-acetamidovinylthio)-9-deoxyclavulanate (e 11) (1.78 g, 4.11 mmole) in dichloromethane (100 ml) was treated dropwise over 10 mins. with a solution of m-chloroperbenzoic acid (1.49 g, 8.63 mmole). The solution was stirred 2 hours at 0°–5° C., washed with 1 N aqueous sodium bicarbonate solution (2×100 ml) and water (100 ml), dried over MgSO$_4$ and evaporated. The residue was chromatographed on silica (60 g), eluting with ethyl acetate to provide p-nitrobenzyl 9-E-(2'-acetamidovinylsulfonyl)-9-deoxyclavulanate (e17) (1.5 g, 79%), identical to the product of Example 12.

EXAMPLE 16

Sodium 9-E-(2'-acetamidovinylsulfonyl)-9-deoxyclavulanate

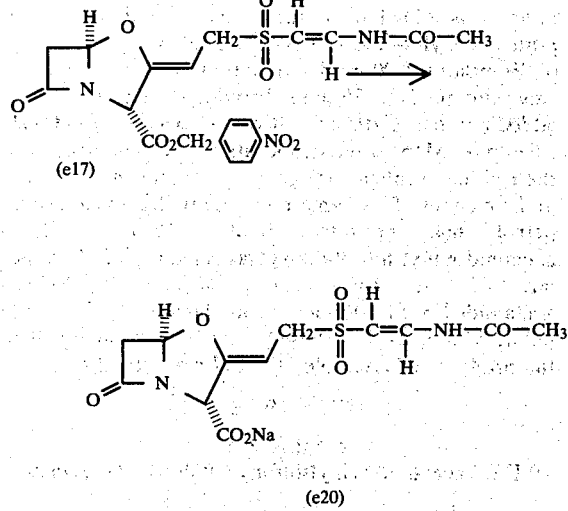

(e17)

(e20)

p-Nitrobenzyl 9-E-(2'-acetamidovinylsulfonyl)-9-deoxyclavulanate (e 17) (0.29 g, 0.642 mmole) was deprotected in an identical manner to that of Example 6, using the same reagent and solvent quantities, to obtain a solution of 9-E-(2'-acetamidovinylsulfonyl)-9-deoxyclavulanic acid in tetrahydrofuran (10 ml). To this was added water (10 ml) and the solution was brought to pH 7 by dropwise addition of 0.1 N aqueous sodium bicarbonate solution. Organic solvent was evaporated at reduced pressure and the remaining aqueous solution was freeze dried to provide sodium 9-E-(2'-acetamidovinylsulfonyl)-9-deoxyclavulanate (e 20) (0.154 g, 70%).

EXAMPLE 17 p-Nitrobenzyl 9-Z-(2'-propionamidovinylthio)-9-deoxyclavulanate and p-nitrobenzyl-9-E-(2'-propionamidovinylthio)-9-deoxyclavulanate

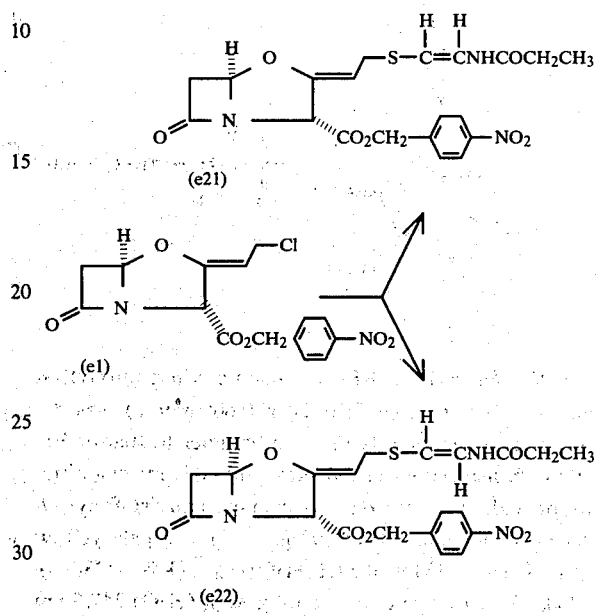

(e21)

(e1)

(e22)

A 1:1 mixture of sodium Z-2-propionamidovinylthiolate and sodium E-2-propionamidovinylthiolate (0.915 g, 4.35 mmole) was added to a stirred, ice-cooled solution of p-nitrobenzyl 9-chloro-9-deoxyclavulanate (e 1) (1.5 g, 4.26 mmole) in dry DMF (50 ml). The mixture was stirred for 40 minutes, diluted with ethyl acetate (200 ml) and washed with water (3×150 ml). The ethyl acetate extract was dried over MgSO$_4$ and evaporated under reduced pressure. The residue was chromatographed on silica (50 g) in the manner of example 1, eluting with ethyl acetate/petrol (2:3), to provide p-nitrobenzyl 9-Z-(2'-propionamidovinylthio)-9-deoxyclavulanate (e 21) (less polar, 0.57 g, 30%, $[\alpha]_D^{20} -21.4°$(c.1.1; CHCl$_3$); $\nu_{max}$ (CHCl$_3$) 3400, 1810, 1755, 1695, 1630 cm$^{-1}$; $\lambda_{max}$ (EtOH) 266 nm (20180); $\delta$(CDCl$_3$) 1.17 (3H, t, J 7.5 Hz, —CH$_2$CH$_3$), 2.30 (2H, q, J 7.5 Hz, —CH$_2$CH$_3$), 3.03 (1H, d, J 17 Hz, 6$\beta$-CH), 3.31 (2H, d, J 8 Hz, 9-CH$_2$), 3.50 (1H, dd, J 17 and 2.5 Hz, 6$\alpha$-CH), 4.71 (1H, dt, J 8 and 1 Hz, 8-CH), 5.09 (1H, broad s, 3-CH), 5.17 (1H, d, J 7.5 Hz, —SCH=), 5.24 (2H, s, —CH$_2$Ar), 5.67 (1H, d, J 2.5 Hz, 5-CH), 7.08 (1H, dd, J 11 and 7.5 Hz, =CHNH—), 7.3–7.7 (3H, m, NH and 2 Ar-H), 8.21 (2H, d, 2 Ar-H) and p-nitrobenzyl 9-E-(2'-propionamidovinylthio)-9-deoxyclavulanate (more polar, 0.39 g, 20%; $[\alpha]_D^{20} -26.4°$(c.1.1; CHCl$_3$); $\nu_{max}$ (CHCl$_3$) 3450, 1805, 1755, 1695, 1620 cm$^{-1}$; $\lambda_{max}$ (EtOH) 240 nm (14590), 271 nm (18670); $\delta$(CDCl$_3$) 1.14 (3H, t, —CH$_2$CH$_3$), 2.24 (2H, q, —CH$_2$CH$_3$), 3.06 (1H, d, J 17 Hz, 6$\beta$-CH), 3.28 (2H, d, J 8 Hz, 9-CH$_2$), 3.48 (1H, dd, J 17 and 2.5 Hz, 6$\alpha$-CH); 4.71 (1H, broad t, J 8 Hz, 8-CH), 5.11 (1H, s, 3-CH), 5.27 (2H, s, —CH$_2$Ar), 5.5–5.8 (2H, m, 5-CH and —SCH=), 6.97 (1H, dd, J 14 and 11 Hz, =CHNH—), 7.4–7.8 (3H, m, NH and 2Ar-H), 8.21 (2H, d, 2Ar-H). Found: C, 53.7; H, 4.9; N, 9.4;

EXAMPLE 18

Lithium 9-Z-(2'-propionamidovinylthio)-9-deoxyclavulanate

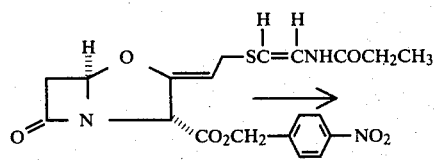
(e21)

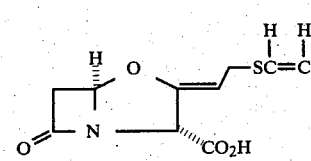
(e23)

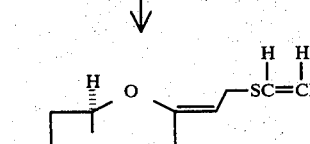
(e24)

p-Nitrobenzyl 9-Z-(2'-propionamidovinylthio)-9-deoxyclavulanate (e 21) (0.284 g; 0.636 mmole) was deprotected in the manner of Example 6, using the same reagent and solvent quantities, to provide lithium 9-Z-(2'-propionamidovinylthio)-9-deoxyclavulanate (e 24) (0.147 g, 72%) as a pale yellow solid. $[\alpha]_D^{20} +74.9°$(c.1.1; $H_2O$). $\nu_{max}$ (KBr) 1770, 1685, 1620 cm$^{-1}$; $\lambda_{max}$ ($H_2O$) 231 nm (12060), 269 nm (11000); $\delta$($D_2O$—HOD≡4.60) 1.07 (3H, t, —$CH_2CH_3$), 2.33 (2H, q, —$CH_2CH_3$), 3.01 (1H, d, J 17 Hz, 6β-C$\underline{H}$), 3.2–3.7 (3H, m, 6α-C$\underline{H}$ and 9-C$\underline{H}_2$), 4.6–5.0 (2H, m partially obscured by HOD, 8-CH and 3-CH), 5.47 (1H, d, J 8 Hz, —SC$\underline{H}$=), 5.66 (1H, d, J 2.5 Hz, 5-C$\underline{H}$), 6.85 (1H, d, J 8 Hz, =C$\underline{H}$NH—).

EXAMPLE 19

Lithium 9-E-(2'-propionamidovinylthio)-9-deoxyclavulanate

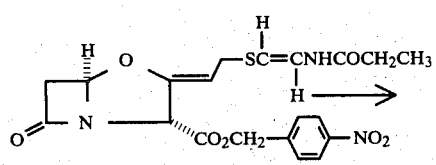
(e22)

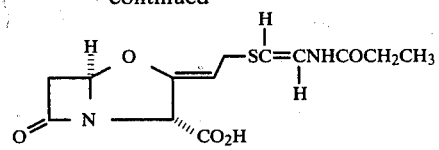

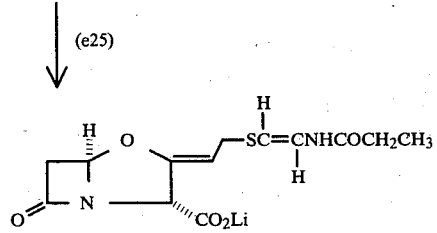
(e26)

p-Nitrobenzyl 9-E-(2'-propionamidovinylthio)-9-deoxyclavulanate (e 22) (0.225 g, 0.504 mmole) was deprotected in the manner of Example 6, using the same reagent and solvent quantities, to provide lithium 9-E-(2'-propionamidovinylthio)-9-deoxyclavulanate (e 26) (0.116 g, 72%) as a white solid. $[\alpha]_D^{20} +171.9°$(c.1.0; $H_2O$); $\nu_{max}$ (KBr) 1770, 1685, 1620 cm$^{-1}$; $\lambda_{max}$ ($H_2O$) 232 nm (10990), 272 nm (10550); $\delta$($D_2O$—HOD≡4.60) 1.05 (3H, t, —$CH_2CH_3$), 2.23 (2H, q, —$CH_2CH_3$), 2.97 (1H, d, J 17 Hz, 6β-C$\underline{H}$), 3.1–3.7 (3H, m, 6α-CH and 9-C$\underline{H}_2$), 4.88 (1H, s, 3-C$\underline{H}$), 5.63 (1H, d, J 2.5 Hz, 5-CH), 5.78 (1H, d, J 14 Hz, —SC$\underline{H}$=), 6.84 (1H, d, J 14 Hz, =C$\underline{H}$NH—), 8-CH obscured by HOD).

EXAMPLE 20 p-Nitrobenzyl-9-Z-(2'-propionamidovinylsulfonyl)-9-deoxyclavulanate

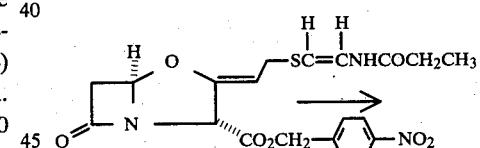
(e21)

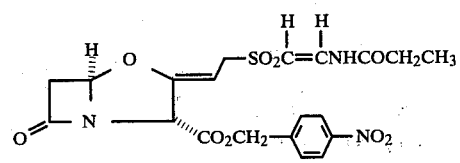
(e27)

A stirred, ice-cooled solution of p-nitrobenzyl 9-Z-(2'-propionamidovinylthio)-9-deoxyclavulanate (e 21) (0.30 g, 0.672 mmole) in dichloromethane (50 ml) was treated dropwise over 10 minutes with a solution of m-chloroperbenzoic acid (0.255 g, 1.48 mmole) in dichloromethane (5 ml). The mixture was stirred at 0°–5° C. for 2.5 hours, washed with 1 N aqueous sodium bicarbonate solution (2×50 ml) and water (50 ml), dried over MgSO$_4$ and evaporated. The residue was chromatographed on silica (30 g) in the manner of Example 1, eluting with ethyl acetate/petrol (1:1), to provide p-nitrobenzyl 9-Z-(2'-propionamidovinylsulfonyl)-9-deoxyclavulanate (e 27) (0.25 g, 78%). White, microcrystalline (ethyl acetate/petrol), m.p. 106°-8° C. $[\alpha]_D^{20} -7.7°$(c.1.1; CHCl$_3$); $\nu_{max}$ (CHCl$_3$) 3380, 1810, 1760, 1725, 1700(s), 1630 cm$^{-1}$; $\lambda_{max}$ (EtOH) 253.5 nm (31080); $\delta$(CDCl$_3$) 1.18 (3H, t, CH$_2$CH$_3$), 2.37 (2H, q, —CH$_2$CH$_3$), 3.07 (1H, d, J 17 Hz, 6$\beta$-CH), 3.54 (1H, dd, J 17 and 2.5 Hz, 6$\alpha$-CH), 3.82 (2H, d, J 8 Hz, 9-CH$_2$), 4.78 (1H, dt, J 8 and 1 Hz, 8-CH), 5.1-5.4 (4H, m, —CH$_2$Ar, 3-CH and —SO$_2$CH=), 5.73 (1H, d, J 2.5 Hz, 5-CH), 7.4-7.7 (3H, m, 2Ar-H and =CHNH—), 8.22 (2H, d, 2Ar-H), 9.68 (1H, d, J 12 Hz, NH). Found: C, 50.2; H, 4.5; N, 8.8; S, 6.5%. Calculated for C$_{20}$H$_{21}$N$_3$O$_9$S C, 50.1; H, 4.4; N, 8.8; S, 6.7%.

EXAMPLE 21

Lithium 9-Z-(2'-propionamidovinylsulfonyl)-9-deoxyclavulanate

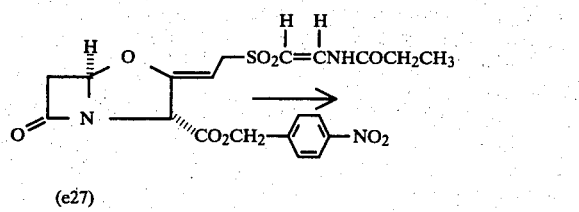

(e27)

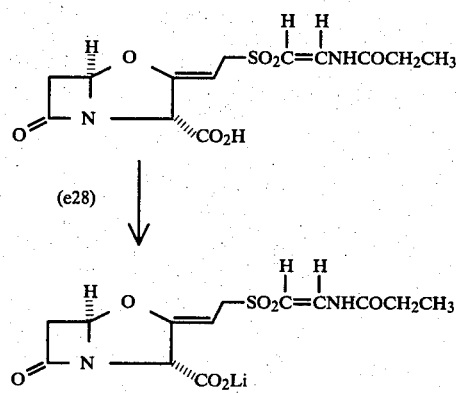

(e28)

(e29)

p-Nitrobenzyl 9-Z-(2'-propionamidovinylsulfonyl)-9-deoxyclavulanate (e 27) (0.19 g, 0.397 mmole) was deprotected in the manner of Example 2, using the same reagent and solvent quantities, to provide lithium 9-Z-(2'-propionamidovinylsulfonyl)-9-deoxyclavulanate (e 29) (0.107 g, 77%) as a yellow solid. $[\alpha]_D^{20}+73.4°$(c.1.1; H$_2$O); $\nu_{max}$ (KBr) 1782, 1690, 1620 cm$^{-1}$; $\lambda_{max}$ (H$_2$O) 225 nm (S) (11580), 251 nm (17900); $\delta$(D$_2$O-HOD=4.61) 1.10 (3H, t —CH$_2$CH$_3$), 2.46 (2H, q, —CH$_2$CH$_3$), 3.06 (1H, d, J 18 Hz, 6$\beta$-CH), 3.57 (1H, dd, J 18 and 2.5 Hz, 6$\alpha$-CH), 3.92 (1H, dd, J 15 and 8 Hz, 9-CH), 4.12 (1H, dd, J 15 and 8 Hz, 9-CH), 4.93 (1H, s, 3-CH), 5.58 (1H, d, J 9.5 Hz-SO$_2$CH=), 5.78 (1H, d, J 2.5 Hz, 5-CH), 7.60 (1H, d, J 9.5 Hz, =CHNH—).

EXAMPLE 22 p-Nitrobenzyl 9-E-(2'-propionamidovinylsulfonyl)-9-deoxyclavulanate

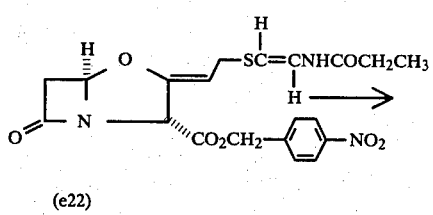

(e22)

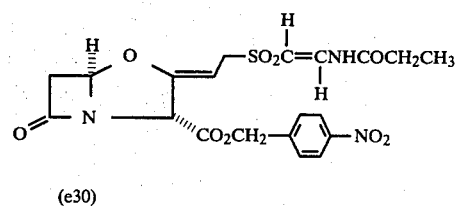

(e30)

A stirred, ice-cooled solution of p-nitrobenzyl-9-E-(2'-propionamidovinylthio)-9-deoxyclavulanate (e 22) (0.25 g, 0.56 mmole) in dichloromethane (50 ml) was treated dropwise over 10 minutes with a solution of m-chloroperbenzoic acid (0.212 g, 1.23 mmole) in dichloromethane (5 ml). The mixture was stirred for 2.5 hours, washed with 1 N aqueous sodium bicarbonate solution (2×50 ml) and water (50 ml) dried over MgSO$_4$ and evaporated. The residue was chromatographed on silica (30 g), eluting with ethyl acetate/petrol (3:1), to provide p-nitrobenzyl 9-E-(2'-propionamidovinylsulfonyl)-9-deoxyclavulanate (e 30) (0.24 g, 89%). White, microcrystalline, m.p., 175°-8° C. $[\alpha]_D^{20}+25.0°$(c.0.9; DMSO); $\nu_{max}$ (CHCl$_3$) 1810, 1760, 1725, 1700(s), 1630 cm$^{-1}$; $\lambda_{max}$ (EtOH) 251.5 nm (36560); $\delta$(DMSO) 1.02 (3H, t, —CH$_2$CH$_3$), 2.28 (2H, q, —CH$_2$CH$_3$), 3.10 (1H, d, J 17 Hz, 6$\beta$—CH), 3.5-4.0 (3H, m, 6$\alpha$-CH and 9-CH$_2$), 4.72 (1H, broad t, J 8 Hz, 8-CH), 5.33 (2H, s, —CH$_2$Ar), 5.50 (1H, s, 3-CH), 5.76 (1H, d, J 2.5 Hz, 5-CH), 5.97 (1H, d, J 13 Hz, —SO$_2$CH=), 7.3-7.8 (3H, m, 2Ar-H and =CHNH), 8.22 (2H, d, 2Ar-H), 10.62 (1H, d, J 11 Hz, NH). Found: C, 50.3; H, 4.3; N, 8.7; S, 6.7%. Calculated for C$_{20}$H$_{21}$N$_3$O$_9$S C, 50.1; H, 4.4; N, 8.8; S, 6.7%.

EXAMPLE 23

Lithium 9-E-(2'-propionamidovinylsulfonyl)-9-deoxyclavulanate

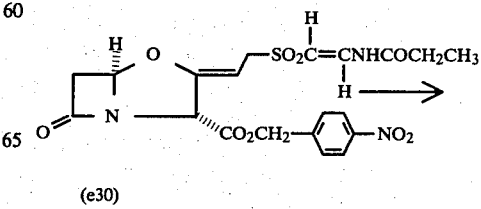

(e30)

-continued

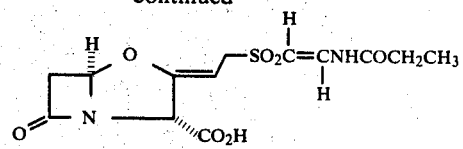

↓ (e31)

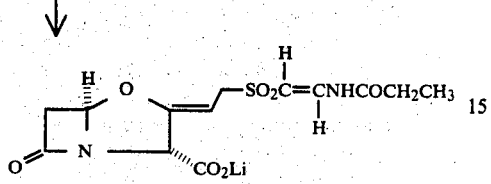

(e32)

p-Nitrobenzyl 9-E-(2′-propionamidovinylsulfonyl)-9-deoxyclavulanate (e30) (0.16 g, 0.334 mmole) was deprotected in the manner of Example 2, using the same reagent and solvent quantities to provide lithium 9-E-(2′-propionamidovinylsulfonyl)-9-deoxyclavulanate (e32) (0.097 g, 83%) as a pale yellow solid. $[\alpha]_D^{20}+124.7°$ (c.1.1; $H_2O$); $\nu_{max}$ (KBr) 1787, 1695, 1620 cm$^{-1}$; $\lambda_{max}$ ($H_2O$) 250 nm (19480); $\delta(D_2O\text{—HOD}=4.60)$, 1.08 (3H, t, —CH$_2$C$\underline{H}_3$), 2.38 (2H, q, —C$\underline{H}_2$CH$_3$), 2.97 (1H, d, J 17 Hz, 6β-C$\underline{H}$), 3.53 (1H, dd, J 17 and 2.5 Hz, 6α-C$\underline{H}$), 3.81 (1H, dd, J 14 and 8 Hz, 9-C$\underline{H}$), 4.04 (1H, dd, J 14 and 8 Hz, 9-C$\underline{H}$), 4.92 (1H, s, 3-C$\underline{H}$), 5.67 (1H, d, J 2.5 Hz, 5-C$\underline{H}$), 6.11 (1H, d, J 14 Hz, —SO$_2$C$\underline{H}$=), 7.54 (1H, d, J 14 Hz, =C$\underline{H}$NH—).

EXAMPLE 24 p-Nitrobenzyl 9-Z-(2′-formamidovinylthio)-9-deoxyclavulanate

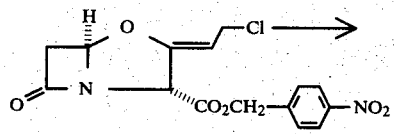

(e1)

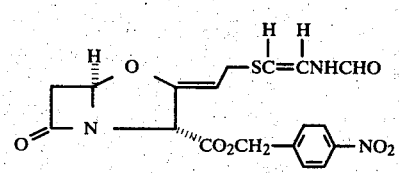

(e33)

Sodium Z-2-formamidovinylthiolate (0.78 g, 4.25 mmole) was added to a stirred, ice-cooled solution of p-nitrobenzyl-9-chloro-9-deoxyclavulanate (e1) (1.50 g, 4.25 mmole) in dry DMF (50 ml). The mixture was stirred 35 minutes, diluted with ethyl acetate (200 ml) and washed with water (3×150 ml). The ethyl acetate was dried over MgSO$_4$ and evaporated under reduced pressure. The residue was chromatographed on silica (40 g) in the manner of Example 1, eluting with ethyl acetate/petrol (1:1), to provide p-nitrobenzyl 9-Z-(2′-formamidovinylthio)-9-deoxyclavulanate (0.495 g, 28%) as a pale yellow oil. $[\alpha]_D^{20}-16.4°$ (c.1.1; CHCl$_3$); $\nu_{max}$ (CHCl$_3$) 3390, 1808, 1758, 1700, 1635 cm$^{-1}$; $\lambda_{max}$ (EtOH) 269 nm (19120); $\delta$(CDCl$_3$) 3.04 (1H, d, J 17 Hz, 6β-C$\underline{H}$), 3.2–3.7 (3H, m, 6α-CH and 9-C$\underline{H}_2$), 4.72 (1H, t, J 8 Hz, 8-C$\underline{H}$), 5.0–5.4 (4H, m, 3-C$\underline{H}$, —SC$\underline{H}$= and —C$\underline{H}_2$Ar), 5.69 (1H, d, J 2.5 Hz, 5-C$\underline{H}$), 6.69 (minor) and 7.10 (major) (1H, 2 dd, J 11.5 and 7.5 Hz, =C$\underline{H}$NH—), 7.4–8.0 (1H, broad hump, N$\underline{H}$), 7.51 (2H, d, 2Ar-$\underline{H}$), 8.1–8.4 (3H, m, 2Ar-$\underline{H}$ and C$\underline{H}$O).

EXAMPLE 25

Sodium 9-Z-(2′-formamidovinylthio)-9-deoxyclavulanate

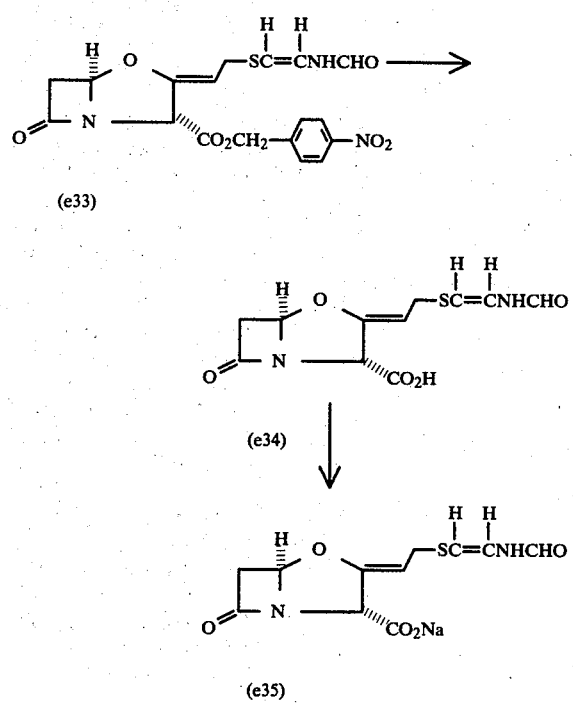

p-Nitrobenzyl 9-Z-(2′-formamidovinylthio)-9-deoxyclavulanate (0.225 g, 0.537 mmole) was deprotected in the manner of Example 6, using the same reagent and solvent quantities except that aqueous sodium bicarbonate instead of lithium carbonate was used to neutralise the free acid (e34). Sodium 9-Z-(2′-formamidovinylthio)-9-deoxyclavulanate was produced as a yellow solid (0.15 g, 92%). $[\alpha]_D^{20}+32.3°$ (c.1.0; $H_2O$); $\nu_{max}$ (KBr) 1780, 1680, 1620 cm$^{-1}$; $\lambda_{max}$ ($H_2O$) 230 nm (9760), 270 nm (8600); $\delta(D_2O\text{—HOD}=4.61)$ 3.02 (1H, d, J 17.5 Hz, 6β-C$\underline{H}$), 3.2–3.7 (3H, m, 6αC$\underline{H}$ and 9-C$\underline{H}_2$), 4.87 (1H, s, 3-C$\underline{H}$), 5.38 (minor, d, J 8 Hz) and 5.57 (major, dd, J 8 and 1.5 Hz) (1H, —SC$\underline{H}$=), 5.65 (1H, d, J 2.5 Hz, 5-C$\underline{H}$), 6.78 (minor) and 6.92 (major) (1H, 2d, J 8 Hz, =C$\underline{H}$NH), 8.05 (major) and 8.29 (minor) (1H, 2s, —C$\underline{H}$O). 8-C$\underline{H}$ obscured by HOD.

EXAMPLE 26 p-Nitrobenzyl 9-Z-(2'-formamidovinylsulfonyl)-9-deoxyclavulanate

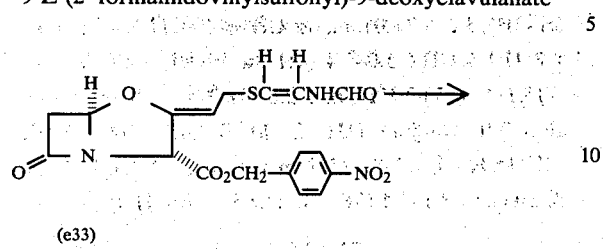

(e33)

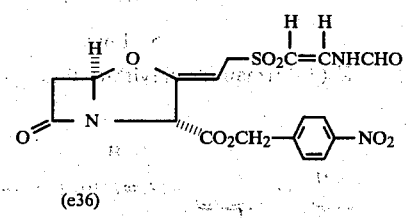

(e36)

A stirred, ice-cooled solution of p-nitrobenzyl-9-Z-(2'-formamidovinylthio)-9-deoxyclavulanate (e33) (0.265 g 0.632 mmole) in dichloromethane (50 ml) was treated dropwise over 10 minutes with a solution of m-chloroperbenzoic acid (0.24 g, 1.39 mmole) in dichloromethane (5 ml). The mixture was stirred at 0°–5° C. for 2 hours, washed with 1 N aqueous sodium bicarbonate solution (2×50 ml) and water (50 ml), dried over MgSO4 and evaporated. The residue was chromatographed on silica (30 g) in the manner of Example 1, eluting with ethyl acetate/petrol (1:1), to provide p-nitrobenzyl 9-Z-(2'-formamidovinylsulfonyl)-9-deoxyclavulanate (e36) (0.23 g, 80%) as a white foam. $[\alpha]_D^{20} -7.0°$ (c.1.1; CHCl3); $\nu_{max}$ (CHCl3) 3360, 1812, 1760, 1730, 1700(s), 1635 cm$^{-1}$; $\lambda_{max}$ (EtOH) 253 nm (18250); δ(CDCl3) 3.08 (1H, d, J 17 Hz, 6β-C$\underline{H}$), 3.56 (1H, dd, J 17 and 2.5 Hz, 6α-C$\underline{H}$), 3.84 (2H, d, J 8 Hz, 9-C$\underline{H}_2$), 4.79 (1H, t, J 8 Hz, 8-C$\underline{H}$), 5.21 (1H, s, 3-C$\underline{H}$), 5.28 (2H, s, —C$\underline{H}_2$Ar), 5.43 (1H, d, J 10 Hz, —SO2C$\underline{H}$=), 5.74 (1H, d, J 2.5 Hz, 5-C$\underline{H}$), 7.4–7.8 (3H, m, 2Ar-$\underline{H}$ and =C$\underline{H}$NH—), 8.1–8.4 (3H, m, 2Ar-$\underline{H}$ and C$\underline{H}$O), 9.78 (1H, d, J 12 Hz, N$\underline{H}$).

EXAMPLE 27

Lithium 9-Z-(2'-formamidovinylsulfonyl)-9-deoxyclavulanate

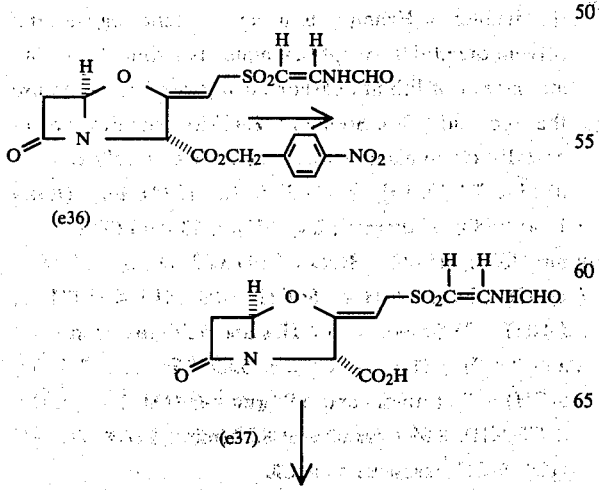

(e36)

(e37)

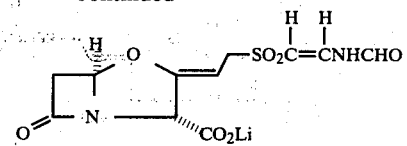

(e38)

p-Nitrobenzyl 9-Z-(2'-formamidovinylsulfonyl)-9-deoxyclavulanate (e36) (0.236 g, 0.523 mmole) was deprotected in the manner of Example 6, using the same reagent and solvent quantities, to provide lithium 9-Z-(2'-formamidovinylsulfonyl)-9-deoxyclavulanate (e38) as a yellow solid (0.145 g, 86%). $[\alpha]_D^{20} +39.4°$ (c.1.0; H2O); $\nu_{max}$ (KBr) 1785, 1700, 1625 cm$^{-1}$; $\lambda_{max}$ (H2O) 230 nm(S) (11270), 248 (14330); (D2O-HOD≡4.61) 3.03 (1H, d, J 17.5 Hz, 6β-C$\underline{H}$), 3.53 (1H, dd, J 17.5 and 2.5 Hz, 6α-C$\underline{H}$), 3.97 (2H, d, J 8 Hz, 9-C$\underline{H}_2$), 4.89 (1H, s, 3-C$\underline{H}$), 5.3–5.8 (2H, m, —SO2C$\underline{H}$= and 5-C$\underline{H}$), 7.30 (minor) and 7.54 (major) (1H, 2d, J 9.5 Hz, =C$\underline{H}$NH), 8.17 (major) and 8.28 (minor) (1H, 2s, C$\underline{H}$O), 8-CH obscured by HOD.

EXAMPLE 28 p-Nitrobenzyl 9-E-(2'-formamidovinylthio)-9-deoxyclavulanate

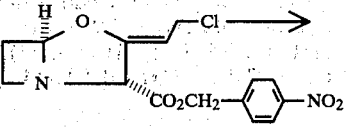

(e1)

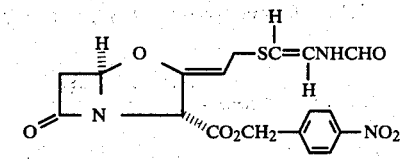

(e39)

Sodium E-2-formamidovinylthiolate (0.41 g, 2.23 mmole) was added to a stirred, ice-cooled solution of p-nitrobenzyl-9-chloro-9-deoxyclavulanate (0.788 g, 2.23 mmole) in dry DMF (25 ml). The mixture was stirred 45 minutes at 0°–5° C., diluted with ethyl acetate (150 ml) was washed with water (3×100 ml). The ethyl acetate solution was dried over MgSO4 and evaporated. Chromatography of the residue on silica (30 g) in the manner of Example 1, eluting with ethyl acetate/petrol (3:2), provided p-nitrobenzyl 9-E-(2'-formamidovinylthio)-9-deoxyclavulanate (e39) as a colourless oil (0.28 g, 30%). $[\alpha]_D^{20} -9.2°$ (c.1.2; CHCL3); $\nu_{max}$ (CHCl3) 3430, 1807, 1755, 1695, 1630 cm$^{-1}$; $\lambda_{max}$(EtOH) 277 nm (15530); δ(CDCl3) 2.9–3.7 (4H, m, 6-C$\underline{H}_2$ and 9-C$\underline{H}_2$), 4.72 (1H, t, J 8 Hz, 8-C$\underline{H}$), 5.13 (1H, s, 3-C$\underline{H}$), 5.29 (2H, s, —C$\underline{H}_2$Ar), 5.4–6.0 (;b 2H, m, 5-CH and —SC$\underline{H}$=), 6.59 (minor) and 6.89 (major) (1H, 2dd, J 14 and 10.5 Hz, =C$\underline{H}$NH—), 7.51 (2H, d, 2Ar-$\underline{H}$), 8.05 (1l H, s, —C$\underline{H}$O), 8.22 (2H, d, 2Ar-$\underline{H}$), 7–8.5 (1H, very broad, N$\underline{H}$).

EXAMPLE 29

Lithium 9-E-(2-formamidovinylthio)-9-deoxyclavulanate

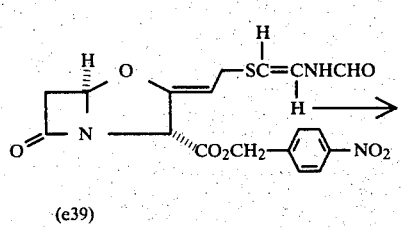

(e39)

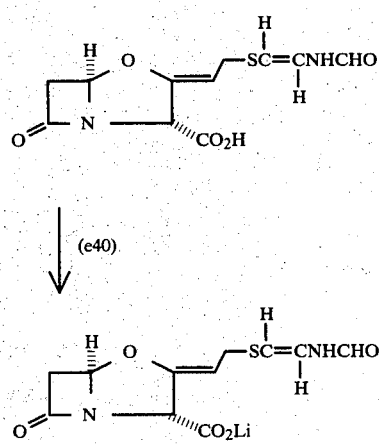

p-Nitrobenzyl 9-E-(2'-formamidovinylthio)-9-deoxyclavulanate (e39) (0.12 g, 0.286 mmole) was deprotected in the manner of Example 2, using the same reagent and solvent quantities, to provide lithium 9-E-(2'-formamidovinylthio)-9-deoxyclavulanate (e41) (0.05 g, 60%). $[\alpha]_D^{20}+108.7°$ (c.0.9; $H_2O$); $\nu_{max}$(KBr) 1780, 1675, 1625 cm$^{-1}$; $\lambda_{max}$ ($H_2O$) 227 nm (11820), 271 nm (9370); δ($D_2O$—HOD=4.61) 2.97 (minor) and 3.00 (major) (1H, 2d, J 17 Hz, 6β-CH), 3.1-3.7 (3H, m, 6α-C$\underline{H}$ and 9-C$\underline{H}_2$), 4.5-5.1 (2H and HOD, m, 8-C$\underline{H}$ and 3-C$\underline{H}$), 5.64 (1H, d, J 2.5 Hz, 5-C$\underline{H}$), 5.68 (minor) and 5.93 (major) (1H, 2 d, J 14 Hz, —SC$\underline{H}$=), 6.73 (minor) and 6.83 (major) (1H, 2d, J 14 Hz, =C$\underline{H}$NH—), 7.91 (major) and 8.17 (minor) (1H, 2s, C$\underline{H}$O).

EXAMPLE 30 p-Nitrobenzyl 9-E-(2'-formamidovinylsulfonyl)-9-deoxyclavulanate

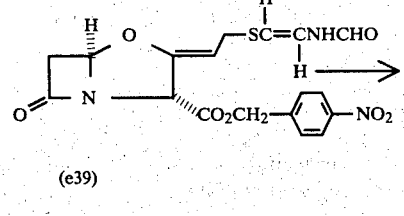

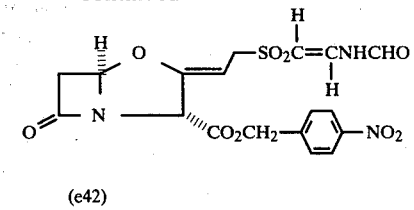

(e42)

A stirred, ice-cooled solution of p-nitrobenzyl-9-E-(2'formamidovinylthio)-9-deoxyclavulanate (e39) (0.17 g, 0.405 mmole) in dichloromethane (20 ml) was treated dropwise over 2 minutes with a solution of m-chloroperbenzoic acid (0.154 g, 0.89 mmole) in dichloromethane at 0°-5° C. (5 ml). The mixture was stirred for 1.5 hours, washed with 1 N aqueous sodium bicarbonate solution (2×20 ml) and water (20 ml), dried over $MgSO_4$ and evaporated. The residue was chromatographed on silica (25 g) in the manner of Example 1, eluting with ethyl acetate/petrol (3:1), to provide p-nitrobenzyl 9-E-(2'-formamidovinylsulfonyl)-9-deoxyclavulanate (e42) (0.13 g, 71%). $[\alpha]_D^{20}-8.4°$ (c.1.0; $CHCl_3$); $\nu_{max}$ ($CHCl_3$), 1810, 1757, 1728, 1700(s), 1640 cm$^{-1}$; $\nu_{max}$ (EtOH) 250 nm (19900); δ($CDCl_3$) 3.08 (1H, d, J 17 Hz, 6β-CH), 3.56 (1H, dd, J 17 and 2.5 Hz, 6α-C$\underline{H}$), 3.84 (2H, d, J 8 Hz, 9-C$H_2$) 4.79 (1H, t, J 8 Hz, 8-C$\underline{H}$), 5.21 (1H, s, 3-C$\underline{H}$), 5.28 (2H, s, —C$\underline{H}_2$Ar), 5.43 (1H, d, J 10 Hz, —$SO_2$C$\underline{H}$=), 5.74 (1H, d J 2.5 Hz, 5-C$\underline{H}$), 7.4-7.8 (3H, m, 2 Ar-$\underline{H}$ and =C$\underline{H}$NH—), 8.1-8.4 (3H, m, 2 Ar-H and C$\underline{H}$O), 9.78 (1H, d, J 12 Hz, N$\underline{H}$).

EXAMPLE 31

Lithium 9-E-(2'-formamidovinylsulfonyl)-9-deoxyclavulanate

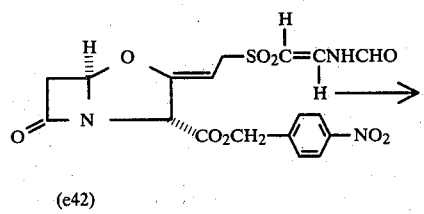

(e42)

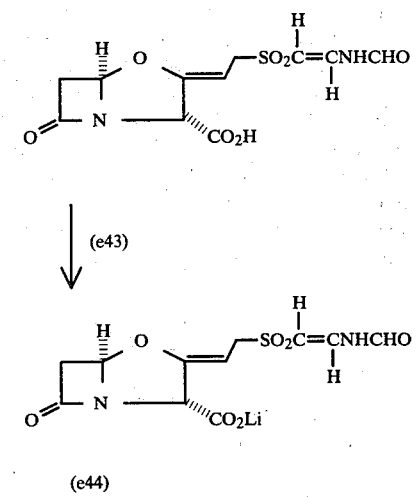

(e44)

p-Nitrobenzyl 9-E-(2'-formamidovinylsulfonyl)-9-deoxyclavulanate (e42) (0.115 g, 0.255 mmole) was deprotected in the manner of Example 2, using the same reagent and solvent quantities, to provide lithium 9-E-(2'-formamidovinylsulfonyl)-9-deoxyclavulanate (e44) (0.035 g, 43%). $[\alpha]_D^{20}+28.6°$ (c.0.9; $H_2O$); $\nu_{max}$ (KBr) 1785, 1695, 1630 cm$^{-1}$; $\lambda_{max}(H_2O)$ 242 nm (14870); $\delta(D_2O-HOD=4.61)$ 3.00 (1H, d, J 17.5 Hz, 6β-C$\underline{H}$), 3.54 (1H, dd, J 17.5 and 2.5 Hz, 6α-C$\underline{H}$), 3.94 (2H, d, J 8 Hz, 9-CH$_2$), 5.67 (1H, d, J 2.5 Hz, 5-CH), 6.33 (major) (<1H, d, J 14 Hz, —SO$_2$C$\underline{H}$=), 7.51 (major) (<1H, d, J 14 Hz, Hz, =CHNH—), 8.26 (major) and 8.40 (minor) (1H, 2s, C$\underline{H}$O).

EXAMPLE 32

Displacement of p-nitrobenzyl-9-O-dichloroacetyl clavulanate by sodium acetamido vinyl thiolate

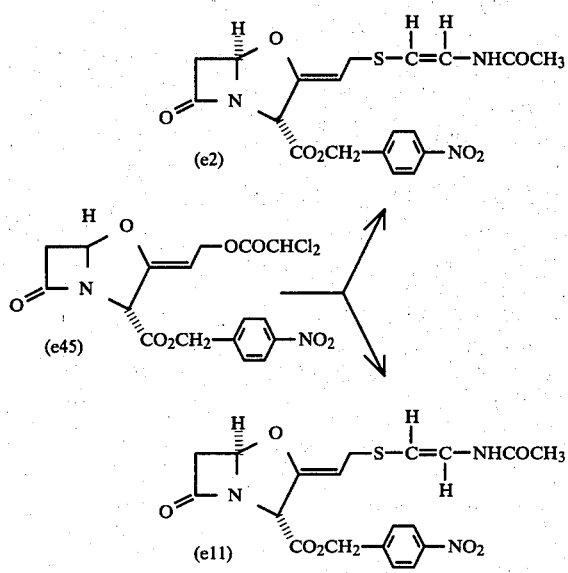

A 1:1 mixture of sodium Z-2-acetamidovinyl thiolate and sodium E-2-acetamidovinyl thiolate (0.49 g; 2.48 mmole) was dissolved in dry dimethylformamide (10 ml) and added dropwise to a stirred, ice-cooled solution of p-nitrobenzyl-9-O-dichloroacetyl clavulanate (e45) (1 g; 2.25 mmole) in dry dimethylformamide (10 ml). The mixture was stored at 0°–5° for 45 minutes, diluted with ethyl acetate (100 ml), washed with water (3×100 ml), dried over anhydrous magnesium sulphate and evaporated. Chromatography of the residue on silica (35 g) in the manner described in Example 1 provided p-nitrobenzyl 9-Z-(2'-acetamidovinylthio)-9-deoxyclavulanate (e2) (0.208 g; 21%) as the less polar product, and p-nitrobenzyl-9-E-(2'-acetamidovinylthio)-9-deoxyclavulanate (e11) (0.136 g; 14%) as the more polar product. These products are identical in all respects to the products of Examples 1 and 7 respectively.

COMPOSITIONS (a) Sterile sodium 9-E-(2'-acetamidovinylsulfonyl)-9-deoxyclavulanate (100 mg) may be filled into glass vials and sealed. The contents may be dissolved in sterile water for injection BP (1.5 ml) to provide an injectable solution.

(b) A two part hard gelating capsule may be filled with a mixture of sodium 9-E-(2'-acetamidovinylsulfonyl)-9-deoxyclavulanate (125 mg) and amoxycillin trihydrate (250 mg).

PREPARATION 1

Sodium-Z-2-acetamidovinylthiolate (a) 2-(2',2'-Diethoxyethylthio)acetamide

Sodium (0.878 g) was dissolved in absolute ethanol (150 ml) under an inert atmosphere. Thioglycolamide (3.47 g) (prepared as described by Sokol and Ritter, J.A.C.S. 70 3517 (1948)) was added and, when practically all the amide had dissolved, bromoacetaldehyde diethyl acetal (11.5 ml) was added. The mixture was heated at 60°–65° C. for 7 hours, cooled and filtered, and the filtrate evaporated under reduced pressure. The residue was dissolved in ethyl acetate (100 ml) and brine (50 ml), the layers separated and the brine extracted with ethyl acetate (50 ml). The combined ethyl acetate extracts were dried over Na$_2$SO$_4$ and evaporated under reduced pressure to yield an oil. Chromatography on silica (50 g), eluting with ethyl acetate/petrol, provided the title compound (6 g) as an oil. $\nu_{max}$ (CHCl$_3$) 3500, 3400 and 1690 cm$^{-1}$; $\delta$(CDCl$_3$) 1.20 (6H, t, J 7 Hz, —CH$_2$C$\underline{H}_3$), 2.80 (2H, d, J 5 Hz, >CHCH$_2$S—), 3.25 (2H, s, —SCH$_2$CO—), 3.58 (4H, 2q J 7 Hz, —OCH$_2$CH$_3$), 4.62 (1H, t, J 5 Hz, —C$\underline{H}$CH$_2$S—), 7.00 (2H, s, —CONH$_2$); Found 207.0951 (M$^+$) C$_8$H$_{17}$NO$_3$S requires 207.0929.

(b) 2,3-Dihydro-4H-1,4-thiazin-3-one 2-(2',2'-Diethoxyethylthio)acetamide (4 g) was dissolved in benzene (80 ml), p-toluene sulfonic acid (0.01 g) added and the mixture heated under reflux in an inert atmosphere with a Dean and Stark trap for 3 hours. The solvent was evaporated under reduced pressure and the residue chromatographed on silica (50 g), eluting with ethyl acetate/petrol to provide the title compound (80%). White plates, mp 74°–75° C. (ethyl acetate/petrol). $\nu_{max}$ (CHCl$_3$) 3200, 1690, 1635 and 1625 cm$^{-1}$; $\delta$(CDCl$_3$) 3.28 (2H, s, —CH$_2$—), 5.57 (1H, d, J 7 Hz, =C$\underline{H}$.S—), 6.37 (1H, dd, J 7 and 5 Hz, =C$\underline{H}$.N—), 9.13 (1H, broad s, NH). $\lambda_{max}$ (EtOH) 230 nm (2940) and 302 nm (2690). Found: C, 41.4; H, 4.4; N, 12.1% C$_4$H$_5$NOS requires C, 41.7; H, 4.35; N, 12.2%.

(c) Sodium Z-2-acetamidovinylthiolate 2,3-Dihydro-4H-1,4-thiazin-3-one (1.61 g, 0.014 mole) was dissolved with stirring in liquid ammonia (100 ml) and treated with sodium (0.645 g, 0.028 mole), added in small pieces over 20 mins. The mixture was stirred a further 15 mins. and treated with solid ammonium chloride (0.748 g, 0.014 mole) portionwise over 5 mins. The ammonia was evaporated, the last traces being removed at 40° C. under vacuum, to provide the title compound mixed with one equivalent of sodium chloride (2.66 g, 96%) as an off white, hygroscopic solid. $\delta$(D$_2$O—HOD at 4.61), 2.05 (3H, s, —COCH$_3$), 5.94 (1H, d, J 7.5 Hz, —SCH=), 6.62 (1H, d, J 7.5 Hz, =C$\underline{H}$NH—).

PREPARATION 2

E-Z mixture of sodium 2-acetamidovinylthiolates (a) 1,1-diethoxy-2-ethylthioethane Sodium (10.7 g, 0.463 mole) was dissolved in ethanol (500 ml) and ice cooled. Ethanethiol (34.4 ml, 0.463 mole) was added, followed after 15 mins. by bromoacetaldehyde diethylacetal (83.8 g, 0.421 mole). The mixture was refluxed 3 hours and the volume reduced to 200 ml by distillation of some of the ethanol at atmospheric pressure. Ether (500 ml) was added and the solution washed with water (3×200 ml), dried over MgSO₄ and evaporated at atmospheric pressure. The residue was distilled to provide title compound (70.46 g, 99%) bp 96°–100° C./20 mm Hg.

(b) E-Z mixture of (2-acetamidovinyl)ethyl sulfides

A mixture of 1,1-diethoxy-2-ethylthioethane (10 g, 0.0595 mole), p-toluene sulfonic acid monohydrate (11.3 g, 0.0595 mole), and acetamide (17.5 g, 0.3 mole) in DMF (250 ml) was stirred at 90° C. for 3 hours. The solvent was evaporated at 50° C. under reduced pressure, the residue taken up in ethyl acetate (600 ml), and washed with water (3×100 ml). The combined water washings were re-extracted with ethyl acetate (200 ml) and the combined ethyl acetate dried over MgSO₄ and evaporated under reduced pressure. The residue was chromatographed on silica (80 g), eluting with ethyl acetate/petrol 2:1 to provide the title compounds as an approximately 1:1 mixture (2.9 g, 33%). $\nu_{max}$ (CHCl₃) 3420, 1690 and 1630 cm⁻¹; $\delta$(CDCl₃) 1.25 and 1.28 (3H, 2t, —SCH₂C$\underline{H}$₃), 2.03 and 2.11 (3H, 2s, —COCH₃), 2.59 and 2.64 (2H, 2q, —SC$\underline{H}$₂CH₃), 5.31 (d, J 7.5 Hz, —SC$\underline{H}$= of Z isomer) and 5.74 (d, J 14 Hz, —SC$\underline{H}$= of E isomer), 6.8–7.3 (1H, m, =C$\underline{H}$NH— both isomers), 7.8 and 8.95 (1H, 2 broad peaks, NH).

(c) E-Z mixture of sodium 2-acetamidovinylthiolates

An E-Z mixture of (2-acetamidovinyl)ethyl sulfides (4.5 g, 0.031 mole) was dissolved in liquid ammonia (200 ml) and treated with sodium (1.43 g, 0.062 mole), added in small pieces over 20 mins. The resulting yellow solution was stirred a further 15 mins., treated with ammonium chloride (1.66 g, 0.031 mole) portionwise over 5 mins. and the solvent evaporated. The last traces of ammonia were removed at 40° C. under vacuum to provide the title compounds, mixed with one equivalent of sodium chloride, as a buff coloured hygroscopic solid (6.13 g, 100%). $\delta$(D₂O —HOD at 4.61) 1.91 and 2.05 (3H, 2s, —COCH₃), 5.94 (d, J 7.5 Hz, —SC$\underline{H}$= of Z isomer), 6.25 (d, J 14 Hz, —SC$\underline{H}$= of E isomer), 6.59 (d, J 14 Hz, =C$\underline{H}$NH— of E isomer), 6.63 (d, J 7.5 Hz, =C$\underline{H}$NH— of Z isomer).

PREPARATION 3

E-Z mixture of sodium 2-propionamidovinylthiolates (a) E-Z mixture of ethyl (2-propionamidovinyl) sulfides A mixture of 1,1-diethoxy-2-ethylthioethane (5 g, 0.0298 mole), propionamide (7.31 g, 0.1 mole) of p-toluene sulfonic acid monohydrate (1.37 g, 0.0072 mole) in DMF (130 ml) was stirred at 90° C. for 2 hours. The solvent was evaporated at 50° C. under reduced pressure, the residue taken up in ethyl acetate (300 ml) and washed with water (3×100 ml). The combined water washings were re-extracted with ethyl acetate (100 ml), these combined ethyl acetate extracts were dried over MgSO₄ and evaporated. The residue was chromatographed on silica (50 g) eluting with ethyl acetate/petrol (1:1), to provide the title compounds as an approximately 1:1 mixture (2.20 g, 46%). $\delta$(CDCl₃) 1.0–1.5 (6H, m, 2×—CH₂C$\underline{H}$₃), 2.0–2.9 (4H, m, 2×—C$\underline{H}$₂CH₃), 5.32 (d, J 7.5 Hz, —SC$\underline{H}$= of Z isomer) and 5.77 (d, J 14 Hz, —SC$\underline{H}$= of E isomer), 6.8–7.3 (1H, m, =C$\underline{H}$NH— of both isomers), 7.7 and 8.6 (1H, 2 broad peaks, NH).

(b) E-Z mixture of sodium 2-propionamidovinylthiolates

An E-Z mixture of ethyl (2-propionamidovinyl) thiolates (3.50 g, 0.022 mole) was dissolved in liquid ammonia (250 ml) and treated with sodium (1.01 g, 0.044 mole), added as small pieces over 15 minutes. The resulting solution was stirred for a further 5 minutes, treated with ammonium chloride (1.18 g, 0.022 mole) and the solvent evaporated. When evaporation was almost complete and the residue a semi-solid mass, dry ether (200 ml) was added and the resulting solid triturated and filtered off. After desiccation, the title compound was obtained as a buff, hygroscopic solid, mixed with one equivalent of sodium chloride (4.62 g, 99%). $\delta$(D₂O—HOD=4.60) 0.9–1.4 (6H, m, 2×—CH₂C$\underline{H}$₃), 1.9–2.7 (4H, m, 2×—C$\underline{H}$₂CH₃), 5.98 (d, J 7.5 Hz, —SC$\underline{H}$= of Z isomer), 6.29 (d, J 14 Hz, —SC$\underline{H}$= of E isomer), 6.4–6.8 (1H, m, =C$\underline{H}$NH— of both isomers).

PREPARATION 4

E-Z sodium 2-formamidovinylthiolates (a) E and Z ethyl (2-formamidovinyl) sulfides A mixture of 1, 1-diethoxy-2-ethylthioethane (5 g, 0.0298 mole), formamide (6.7 g, 0.149 mole) and p-toluene sulfonic acid monohydrate (5.0 g, 0.0263 mole) in DMF (120 ml) was stirred at 90° C. for 4 hours. The solvent was evaporated at 50° C. under reduced pressure and saturated brine (100 ml) was added to the residue. This mixture was extracted with ethyl acetate (3×100 ml), the combined extracts dried over MgSO₄ and evaporated. The residue was chromatographed on silica (50 g), eluting with ethyl acetate/petrol (1:2), to provide the less polar Z-ethyl (2-formamidovinyl) sulfide (0.99 g, 25%) and the more polar E-ethyl (2-formamidovinyl) sulfide (0.75 g, 19%).

Z isomer-$\nu_{max}$ (CHCl₃) 3400, 1695, 1635 cm⁻¹; $\lambda_{max}$ (EtOH) 238 nm (7610), 271 nm (13350); $\delta$(CDCl₃) 1.28 (3H, t, —CH₂C$\underline{H}$₃), 2.67 (2H, q, —C$\underline{H}$₂CH₃), 5.2–5.6 (1H, m, —SC$\underline{H}$=), 6.74 (minor) and 7.19 (major) (1H, 2dd, J 7.5 and 11.5 Hz, =C$\underline{H}$NH), 7.0–9.0 (1H, broad hump, N$\underline{H}$), 8.2–8.6 (1H, m, C$\underline{H}$O).

E isomer-$\nu_{max}$ (CHCl₃) 3450, 1695, 1635 cm⁻¹; $\lambda_{max}$ (EtOH) 232 nm (8010), 274 nm (13250); $\delta$(CDCl₃), 1.27 (3H, t, CH₂C$\underline{H}$₃), 2.61 (minor) and 2.63 (major) (2H, 2q, —C$\underline{H}$₂CH₃), 5.73 (minor) and 5.91 (major) (1H, 2 d, J 14 Hz, —SC$\underline{H}$=), 6.54 (minor) and 6.96 (major) (1H, 2dd, J 14 and 10.5 Hz, =C$\underline{H}$NH—), 7.7–9.0 (2H, m, N$\underline{H}$ and C$\underline{H}$O).

(b) Z-Sodium 2-formamidovinylthiolate

Z-Ethyl (2-formamidovinyl) sulfide (0.956 g, 7.3 mmole) was dissolved in liquid ammonia (100 ml) and treated with small pieces of sodium (0.336 g, 14.6 mmole) over 10 minutes. After all the sodium had dissolved, the mixture was treated with ammonium chloride (0.39 g, 7.3 mmole) and the solvent evaporated until a semi-solid mass was left. Dry ether (100 ml) was added, the solid triturated, filtered off and desiccated to provide the title compound as an off white solid mixed with one equivalent of sodium chloride (1.34 g, 100%). $\nu_{max}$ (KBr) 1675, 1620, 1605 cm⁻¹; $\lambda_{max}$ (H₂O) 231 nm (5110), 287 nm (9620); $\delta$(D₂O—HOD=4.60) 5.83 (minor, d, J 7.5 Hz) and 6.06 (major, dd, J 7.5 and 1.5 Hz) (1H, —SC$\underline{H}$=), 6.5–6.9 (1H, m, =C$\underline{H}$NH—), 8.03 (major) and 8.31 (minor) (1H, 2s, C$\underline{H}$O).

(c) E-Sodium 2-formamidovinylthiolate

E-Ethyl (2-formamidovinyl) sulfide (0.75 g, 5.72 mmole) was dissolved in liquid ammonia (100 ml) and treated with small pieces of sodium (0.264 g, 11.44 mmole) over 10 minutes. When all the sodium had dissolved, the mixture was treated with ammonium chloride (0.306 g, 5.72 mmole) and the solvent evaporated until a semi-solid mass was left. Dry ether (100 ml) was added, the solid triturated, filtered off and desiccated to provide the title compound as a buff, hygroscopic solid mixed with one equivalent of sodium chloride (1.0 g, 95%). $\nu_{max}$ (KBr) 1660 cm$^{-1}$; $\lambda_{max}$ (H$_2$O) 230 nm (4510), 286 nm (10240); $\delta$(D$_2$O—HOD=4.60) 6.3–6.9 (2H, m, —CH=CH—), 7.71 (major) and 8.04 (minor) (1H, 2s, CHO).

DEMONSTRATION 1

Pharmacological Effectiveness

Mice were infected intraperitoneally with mucin suspension of organisms. Dosing was by the subcutaneous route at 1 and 5 hours post-infection. Varying doses of amoxycillin were given with 1, 2 or 5 mg/kg of inhibitor. All 3 strains of infecting organisms were strains producing a plasmid-mediated β-lactamase.

Comparison of Synergistic activity of Compound of Example 13 and Clavulanic acid sodium salt with amoxycillin in acute mouse infections CD$_{50}$ (mg/kg)-subcutaneous dosing at 1 and 5 hours

| Organism | E coli E96 | | | E coli E124 | Kleb. aerog BED6 |
|---|---|---|---|---|---|
| Dose of Inhibitor | 2 mg/kg (3 tests) | | | 1 mg/kg | 2 mg/kg | 5 mg/kg |
| | a | b | c | | | |
| Amoxycillin alone | >1000 | >1000 | >1000 | >1000 | >1000 | >1000 |
| Amoxycillin + sodium clavulanate | 50 | 41 | 13 | 74 | 80 | 11 |
| Amoxycillin + Compound of Example 16 | 12.5 | 6.2 | 6.8 | <12.5 | 22 | 2.7 |

Comparison of Synergistic activity of Compound of Example 6 and Clavulanic acid sodium salt with amoxycillin in acute mouse infections CD$_{50}$ mg/kg-subcutaneous dosing at 1 and 5 hours

| | E coli E96 | |
|---|---|---|
| | a | b |
| Amoxycillin alone | >1000 | >1000 |
| Amoxycillin + sodium clavulanate 2 mg/kg | 35 | 24 |
| Amoxycillin + Compound of Example 6 2 mg/kg | 10 | 9 |

What we claim is:
1. A compound of the formula (I):

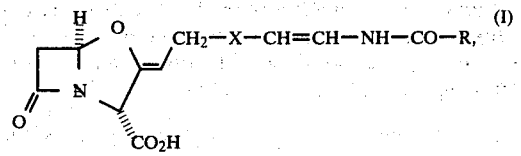

a pharmaceutically acceptable salt thereof,
the p-nitrobenzyl ester thereof or an ester thereof of the formula

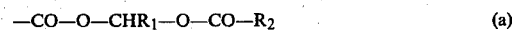

wherein R$_1$ is hydrogen, methyl or phenyl; R$_2$ is alkyl of 1 to 6 carbon atoms, phenyl, alkyl of 1 to 3 carbon atoms mono-substituted by phenyl, alkoxy of 1 to 6 carbon atoms, phenoxl or alkoxyl of 1 to 3 carbon atoms mono-substituted by phenyl; or R$_1$ and R$_2$ together with the —CH—O—CO— form a phthalidyl or 3,4-dimethoxyphthalidyl moiety, wherein R is hydrogen or alkyl of 1 to 6 carbon atoms, and X is a sulphur atom, SO or SO$_2$.

2. A compound according to claim 1 wherein X is a sulphur atom.

3. A compound according to claim 1 wherein X is SO$_2$.

4. A compound according to claim 1 wherein the double bond between the —X— and the —NH— groups is in the E-configuration.

5. A compound according to claim 1 wherein R is methyl.

6. The compound according to claim 1 which is 9-E-(2′-Acetamidovinylsulfonyl)-9-deoxyclavulanic acid, a pharmaceutically acceptable salt thereof or an in vivo hydrolysable ester thereof.

7. A method of treating bacterial infections in mammals which comprises administering to a mammal in need thereof an antibacterially effective amount of a compound of the formula (I)

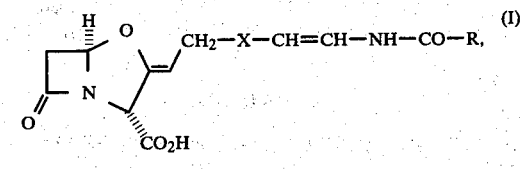

a pharmaceutically acceptable salt thereof,
the p-nitrobenzyl ester thereof or an ester thereof of the formula

wherein R$_1$ is hydrogen, methyl or phenyl; R$_2$ is alkyl of 1 to 6 carbon atoms, phenyl, alkyl of 1 to 3 carbon atoms mono-substituted by phenyl, alkoxy of 1 to 6 carbon atoms, phenoxl or alkoxyl of 1 to 3 carbon atoms mono-substituted by phenyl; or R$_1$ and R$_2$ together with the —CH—O—CO— form a phthalidyl or 3, 4-dimethoxyphthalidyl moiety, wherein R is hydrogen or alkyl of 1 to 6 carbon atoms and X is a sulphur atom, SO or SO$_2$, in combination with a pharmaceutically acceptable carrier.

8. A method according to claim 7 wherein the compound is p-Nitrobenzyl 9-Z-(2′-formamidovinylsulfonyl)-9-deoxyclavulanate.

9. A method according to claim 7 wherein the compound is p-Nitrobenzyl 9-E-(2'-formamidovinylthio)-9-deoxyclavulanate.

10. A method according to claim 7 wherein the compound is p-Nitrobenzyl 9-E-(2'-formamidovinylsulfonyl)-9-deoxyclavulanate.

11. A compound according to claim 1 wherein the double bond between the —X— and the —NH— groups is in the Z-configuration.

12. A compound according to claim 1 wherein R is alkyl of 1 to 6 carbon atoms.

13. A compound according to claim 1 wherein R is methyl, ethyl, n-propyl, isopropyl, n-butyl, t-butyl, sec.-butyl, or iso-butyl.

14. A compound according to claim 1 wherein R is methyl or ethyl.

15. A compound according to claim 1 in the form of the free acid.

16. A compound according to claim 1 in the form of a pharmaceutically acceptable salt.

17. A pharmaceutically acceptable salt according to claim 16 wherein the salt is an alkali metal salt, an alkaline earth metal salt or an ammonium salt.

18. A pharmaceutically acceptable salt according to claim 16 wherein the salt is the sodium, potassium, calcium, magnesium, triethylamine, 2-hydroxyethylamine, bis-(2-hydroxyethyl)amine, tris-(hydroxymethyl)amine, tris-(2-hydroxyethyl)amine, bicyclohexylamine, procaine, dibenzylamine, N,N-dibenzylethyleneediamine, 1-ephenamine, N-ethyl-piperidine, N-benzyl-$\beta$-phenethylamine, dehydroabietylamine, or N,N-bis-dehydroabietylethylenediamine.

19. A compound according to claim 1 in the form of the sodium, potassium, calcium, magnesium or ammonium salt.

20. A method according to claim 7 wherein the compound is p-Nitrobenzyl 9-Z-(2'-formamidovinylthio)-9-deoxyclavulanate.

21. A method according to claim 7 wherein the compound is Sodium 9-Z-(2'-formamidovinylthio)-9-deoxyclavulanate.

22. An ester claim 1 wherein $R_1$ is hydrogen and $R_2$ is methyl, ethyl, n-propyl, isopropyl, n-butyl, tert-butyl, phenyl, benzyl, methoxy, ethoxy, n-propyloxy or isopropyloxy.

23. An ester according to claim 22 wherein $R_2$ is tert-butyl.

24. An ester according to claim 1 wherein $R_1$ and $R_2$ together with the —CH—O—CO— form a phthalidyl or 3,4-dimethoxy phthalidyl moiety.

25. A compound according to claim 1 in the form of the acetoxymethyl, acetoxyethyl, phthalidyl, ethoxycarbonyloxymethyl, α-ethoxycarbonyloxyethyl or pivaloyloxymethyl ester.

26. The compound according to claim 1 which is p-Nitrobenzyl 9-Z-(2'-acetamidovinylthio)-9-deoxy clavulanate.

27. The compound according to claim 1 which is p-Nitrobenzyl 9-Z-(2'-acetamidovinylsulfinyl)-9-deoxy clavulanate.

28. The compound according to claim 1 which is p-Nitrobenzyl 9-Z-(2'-acetamidovinulsulfonyl)-9-deoxyclavulanate.

29. The compound according to claim 1 which is p-Nitrobenzyl 9-E-(2'acetamidovinylthio)-9-deoxyclavulanate.

30. The compound according to claim 1 which is p-Nitrobenzyl 9-E-(2'-acetamidovinylsulfinyl)-9-deoxyclavulanate.

31. A method according to claim 7 wherein the compound is p-Nitrobenzyl 9-Z-(2'-propionamidovinylthio)-9-deoxyclavulanate.

32. A method according to claim 7 wherein the compound is p-Nitrobenzyl-9-E-(2'-propionamidovinylthio)-9-deoxyclavulanate.

33. A method according to claim 7 wherein the compound is p-Nitrobenzyl-9-Z-(2'-propionamidovinylsulfonyl)-9-deoxyclavulanate.

34. A method according to claim 7 wherein the compound is p-Nitrobenzyl 9-E-(2'-propionamidovinylsulfonyl)-9-deoxyclavulanate.

35. The compound according to claim 1 which is p-Nitrobenzyl 9-E-(2'acetamidovinulsulfonyl)-9-deoxyclavulanate.

36. The compound according to claim 1 which is Sodium 9-E-(2'-acetamidovinylsulfonyl)-9-deoxyclavulanate.

37. The compound according to claim 1 which is p-Nitrobenzyl 9-Z-(2'-propionamidovinylthio)-9-deoxyclavulanate.

38. The compound according to claim 1 which is p-Nitrobenzyl-9-E-(2'-propionamidovinylthio)-9-deoxyclavulanate.

39. The compound according to claim 1 which is p-Nitrobenzyl-9-Z-(2'-propionamidovinylsulfonyl)-9-deoxyclavulanate.

40. The compound according to claim 1 which is p-Nitrobenzyl 9-E-(2'-propionamidovinylsulfonyl)-9-deoxyclavulanate.

41. The compound according to claim 1 which is p-Nitrobenzyl 9-Z-(2'-formamidovinylthio)-9-deoxyclavulanate.

42. The compound according to claim 1 which is Sodium 9-Z-(2'-formamidovinylthio)-9-deoxyclavulanate.

43. The compound according to claim 1 which is p-Nitrobenzyl 9-Z-(2'-formamidovinylsulfonyl)-B 9-deoxyclavulanate.

44. The compound according to claim 1 which is p-Nitrobenzyl 9-E-(2'formamidovinylthio)-9-deoxyclavulanate.

45. The compound according to claim 1 which is p-Nitrobenzyl 9-E-(2'-formamidovinylsulfonyl)-9-deoxyclavulanate.

46. A non-pharmaceutically acceptable salt of a compound of the formula (I):

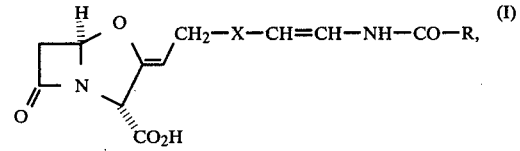

or a pharmaceutically acceptable salt thereof, the p-nitrobenzyl ester thereof or an ester thereof of the formula

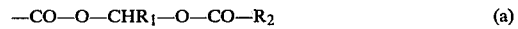

—CO—O—$CHR_1$—O—CO—$R_2$     (a)

wherein $R_1$ is hydrogen, methyl or phenyl; $R_2$ is alkyl of 1 to 6 carbon atoms, phenyl, alkyl of 1 to 3 carbon atoms mono-substituted by phenyl, alkoxy of 1 to 6 carbon atoms, phenoxl or alkoxyl of 1 to 3 carbon atoms mono-substituted by phenyl; or $R_1$ and $R_2$ together with the —CH—O—CO— form a phthalidyl or 3, 4-dimethoxyphthalidyl moiety, wherein R is hydrogen or alkyl of 1 to 6 carbon atoms, and X is a sulphur atom, SO or $SO_2$.

47. A non-pharmaceutically acceptable salt according to claim 46 which is the lithium salt.

48. A method according to claim 7 wherein the compound is Sodium 9-E-(2'acetamidovinylsulfonyl)-9-deoxyclavulanate.

49. The salt according to claim 46 which is Lithium 9-Z-(2'acetamidovinylthio)-9-deoxyclavulanate.

50. The salt according to claim 46 which is Lithium 9-Z-(2'-acetamidovinylsulfinyl)-9-deoxyclavulanate.

51. The salt according to claim 46 which is Lithium 9-Z-(2'acetamidovinylsulfonyl)-9-deoxyclavulanate.

52. A method according to claim 7 wherein the compound is p-Nitrobenzyl 9-E-(2'acetamidovinulsulfonyl)-9-deoxyclavulanate.

53. The salt according to claim 46 which is Lithium 9-E-(2'acetamidovinylthio)-9-deoxyclavulanate.

54. The salt according to claim 46 which is Lithium 9-E-(2'acetamidovinylsulfinyl)-9-deoxyclavulanate.

55. The salt according to claim 46 which is Lithium 9-E-(2'-acetamidovinylsulfonyl)-9-deoxyclavulanate.

56. The salt according to claim 46 which is Lithium 9-Z-(2'-propionamidovinylthio)-9-deoxyclavulanate.

57. The salt according to claim 46 which is Lithium 9-E-(2'-propionamidovinylthio)-9-deoxyclavulanate.

58. The salt according to claim 46 which is Lithium 9-Z-(2'-propionamidovinylsulfonyl)-9-deoxyclavulanate.

59. The salt according to claim 46 which is Lithium 9-E-(2'-propionamidovinylsulfonyl)-9-deoxyclavulanate.

60. The salt according to claim 46 which is Lithium 9-Z-(2'-formamidovinylsulfonyl)-9-deoxyclavulanate.

61. The salt according to claim 46 which is Lithium 9-E-(2-formamidovinylthio)-9-deoxyclavulanate.

62. The salt according to claim 46 which is Lithium 9-E-(2'-formamidovinylsulfonyl)-9-deoxyclavulanate.

63. A pharmaceutical composition useful for treating bacterial infections in mammals which comprises an antibacterially effective amount of the compound of the formula (I):

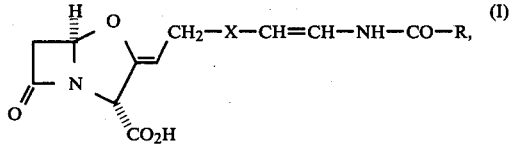

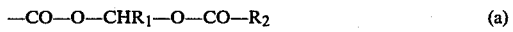

or pharmaceutically acceptable salt thereof, the p-nitrobenzyl ester thereof or an ester thereof of the formula —CO—O—CHR₁—O—CO—R₂        (a)

wherein $R_1$ is hydrogen, methyl or phenyl; $R_2$ is alkyl of 1 to 6 carbon atoms, phenyl, alkyl of 1 to 3 carbon atoms mono-substituted by phenyl, alkoxy of 1 to 6 carbon atoms, phenoxl or alkoxyl of 1 to 3 carbon atoms mono-substituted by phenyl; or $R_1$ and $R_2$ together with the —CH—O—CO— form a phthalidyl or 3, 4-dimethoxyphthalidyl moiety, wherein R is hydrogen or alkyl of 1 to 6 carbon atoms, and X is a sulphur atom, SO or $SO_2$ as the sole antibacterial agent, in combination with a pharmaceutically acceptable carrier.

64. A composition according to claim 63 wherein X is a sulphur atom.

65. A composition according to claim 63 wherein X is $SO_2$.

66. A composition according to claim 63 wherein the double bond between the —X— and the —NH— groups is in the E-configuration.

67. A composition according to claim 63 wherein R is methyl.

68. A composition according to claim 63 wherein the double bond between the —X— and the —NH— groups is in the Z-configuration.

69. A composition according to claim 63 wherein R is alkyl of 1 to 6 carbon atoms.

70. A composition according to claim 63 wherein R is methyl, ethyl, n-propyl, isopropyl, n-butyl, t-butyl, sec.-butyl or iso-butyl.

71. A composition according to claim 63 wherein R is methyl or ethyl.

72. A composition according to claim 63 wherein the compound is in the form of the free acid.

73. A composition according to claim 63 wherein the compound is in the form of a pharmaceutically acceptable salt.

74. A composition according to claim 73 wherein the compound is in the form of a pharmaceutically acceptable salt wherein the salt is an alkali metal salt, an alkaline earth metal salt or an ammonium salt.

75. A composition according to claim 73 wherein the salt is the sodium, potassium, calcium, magnesium, triethylamine, 2-hydroxyethylamine, bis-(2-hydroxyethyl)amine, tris-(hydroxymethyl)amine, tris-(2-hydroxyethyl)amine, bicyclohexylamine, procain, dibenzylamine, N,N-dibenzylethylenediamine, 1-ephenamine, N-ethyl-piperidine, N-benzyl-phenethylamine, dehydroabietylamine of N,N-bis-dehydroabietylethylenediamine.

76. A composition according to claim 73 wherein the salt is the sodium, potassium, calcium, magnesium or ammonium salt.

77. A method according to claim 7 wherein the compound is p-Nitrobenzyl 9-E-(2'-acetamidovinylthio)-9-deoxyclavulanate.

78. A method according to claim 7 wherein the compound is p-Nitrobenzyl 9-E-(2'-acetamidovinylsulfinyl)-9-deoxyclavulanate.

79. A composition according to claim 63 wherein $R_1$ is hydrogen and $R_2$ is methyl, ethyl, n-propyl, isopropyl, n-butyl, tert-butyl, phenyl, benzyl, methoxy, ethoxy, n-propyloxy or isopropyloxy.

80. A composition according to claim 63 wherein $R_2$ is tert-butyl.

81. A composition according to claim 63 wherein $R_1$ and $R_2$ together with the —CH—O—CO— form a phthalidyl or 3, 4-dimethoxy phthalidyl moiety.

82. A composition according to claim 63 wherein the compound is in the form of the acetoxymethyl, acetoxyethyl, phthalidyl, ethoxycarbonyloxymethyl, α-ethoxycarbonyloxyethyl, or pivaloyloxymethyl ester.

83. A composition according to claim 63 wherein the compound is 9-E-(2'-acetamidovinylsulfonyl-9-deoxyclavulanic acid or a pharmaceutically acceptable salt thereof.

84. A composition according to claim 63 wherein the compound is p-Nitrobenzyl 9-Z-(2'-acetamidovinylthio)-9-deoxyclavulanate.

85. A composition according to claim 63 wherein the compound is p-Nitrobenzyl 9-Z-(2'-acetamidovinylsulfinyl)-9-deoxyclavulanate.

86. A composition according to claim 63 wherein the compound is p-Nitrobenzyl 9-Z-(2'-acetamidovinulsulfonyl)-9-deoxyclavulanate.

87. A composition according to claim 63 wherein the compound is p-Nitrobenzyl 9-E-(2'-acetamidovinylthio)-9-deoxyclavulanate.

88. A composition according to claim 63 wherein the compound is p-Nitrobenzyl 9-E-(2'-acetamidovinylsulfinyl)-9-deoxyclavulanate.

89. A method according to claim 7 wherein the compound is 9-E-(2'-acetamidovinylsulfonyl)-9-deoxyclavulanic acid or a pharmaceutically acceptable salt thereof.

90. A method according to claim 7 wherein the compound is p-Nitrobenzyl 9-Z-(2'-acetamidovinylthio)-9-deoxyclavulanate.

91. A method according to claim 7 wherein the compound is p-Nitrobenzyl 9-Z-(2'acetamidovinylsulfinyl)-9-deoxyclavulanate.

92. A method according to claim 7 wherein the compound is p-Nitrobenzyl 9-Z-(2'-acetamidovinylsulfonyl)-9-deoxyclavulanate.

93. A composition according to claim 63 wherein the compound is p-Nitrobenzyl 9-E-(2'acetamidovinulsulfonyl)-9-deoxyclavulanate.

94. A composition according to claim 63 wherein the compound is Sodium 9-E-(2'-acetamidovinylsulfonyl)-9-deoxyclavulanate.

95. A composition according to claim 63 wherein the compound is p-Nitrobenzyl 9-Z-(2'-propionamidovinylthio)-9-deoxyclavulanate.

96. A composition according to claim 63 wherein the compound is p-Nitrobenzyl-9-E-(2'-propionamidovinylthio)-9-deoxyclavulanate.

97. A composition according to claim 63 wherein the compound is p-Nitrobenzyl-9-Z-(2'-propionamidovinylsulfonyl)-9-deoxyclavulanate.

98. A composition according to claim 63 wherein the compound is p-Nitrobenzyl 9-E-(2'-propionamidovinylsulfonyl)-9-deoxyclavulanate.

99. A composition according to claim 63 wherein the compound is p-Nitrobenzyl 9-Z-(2'-formamidovinylthio)-9-deoxyclavulanate.

100. A composition according to claim 63 wherein the compound is Sodium 9-Z-(2'-formamidovinylthio)-9-deoxyclavulanate.

101. A composition according to claim 63 wherein the compound is p-Nitrobenzyl 9-Z-(2'-formamidovinylsulfonyl)-9-deoxyclavulanate.

102. A composition according to claim 63 wherein the compound is p-Nitrobenzyl 9-E-(2'-formaidovinylthio)-9-deoxyclavulanate.

103. A composition according to claim 63 wherein the compound is p-Nitrobenzyl 9-E-(2'-formamidovinylsulfonyl)-9-deoxyclavulanate.

104. A method according to claim 7 wherein the compound is in the form of the acetoxymethyl, acetoxyethyl, phthalidyl, ethoxycarbonyloxymethyl, $\alpha$-ethoxycarbonyloxyethyl, or pivaloyloxymethyl ester.

105. A method according to claim 7 wherein X is a sulphur atom.

106. A method according to claim 7 wherein X is $SO_2$.

107. A method according to claim 7 wherein the double bond between the —X— and the —NH— groups is in the E-configuration.

108. A method according to claim 7 wherein R is methyl.

109. A method according to claim 7 wherein the double bond between the —X— and the —NH— groups is in the Z-configuration.

110. A method according to claim 7 wherein R is alkyl of 1 to 6 carbon atoms.

111. A method according to claim 7 wherein R is methyl, ethyl, n-propyl, isopropyl, n-butyl, t-butyl, sec.-butyl or iso-butyl.

112. A method according to claim 7 wherein R is methyl or ethyl.

113. A method according to claim 7 wherein the compound is in the form of the free acid.

114. A method according to claim 7 wherein the compound is in the form of a pharmaceutically acceptable salt.

115. A method according to claim 114 wherein the compound is form of a pharmaceutically acceptable salt wherein the salt is an alkali metal salt, an alkaline earth metal salt and ammonium salt or a substituted ammonium salt.

116. A method according to claim 114 wherein the salt is the sodium, potassium, calcium, magnesium, triethylamine, 2-hydroxyethylamine, bis-(2-hydroxyethyl)amine, tris-(hydroxymethyl)amine, tris-(2-hydroxyethyl)amine, bicyclohexylamine, procain, dibenzylamine, N,N-dibenzylethylenediamine, 1-ephenamine, N-ethyl-piperidine, N-benzyl-phenethylamine, dehydroabietylamine of N,N-bis-dehydroabietylethylenediamine.

117. A method according to claim 114 wherein the salt is in the form of the sodium, potassium, calcium, magnesium or ammonium salt.

118. A method according to claim 7 wherein $R_2$ is tert-butyl.

119. A method according to claim 7 wherein $R_1$ and $R_2$ together with the —CH—O—CO— form a phthalidyl or 3,4-dimethoxy phthalidyl moiety.

120. A method according to claim 7, wherein $R_1$ is hydrogen and $R_2$ is methyl, ethyl, n-propyl, isopropyl, n-butyl, tert-butyl, phenyl, benzyl, methoxy, ethoxy, n-propyloxy or isopropyloxy.

* * * * *